United States Patent [19]

Gehret

[11] Patent Number: 4,920,148
[45] Date of Patent: Apr. 24, 1990

[54] INSECTICIDES AND PARASITICIDES

[75] Inventor: Jean-Claude Gehret, Aesch, Switzerland

[73] Assignee: Ciba-Geigy Corporation, Ardsley, N.Y.

[21] Appl. No.: 369,436

[22] Filed: Jun. 21, 1989

Related U.S. Application Data

[62] Division of Ser. No. 160,237, Feb. 25, 1988, Pat. No. 4,855,317.

[30] Foreign Application Priority Data

Mar. 6, 1987 [CH] Switzerland ............................ 847/87

[51] Int. Cl.$^5$ ................... A61K 31/365; C07D 493/22
[52] U.S. Cl. ..................................... 514/450; 514/63; 549/264; 549/214
[58] Field of Search ................ 549/264, 214; 514/450, 514/63; 536/7.1

[56] References Cited

U.S. PATENT DOCUMENTS 4,791,134 12/1988 Burckhardt .................. 549/264

Primary Examiner—Richard L. Raymond
Assistant Examiner—Mark W. Russell
Attorney, Agent, or Firm—Edward McC. Roberts

[57] ABSTRACT

The present invention relates to novel C(29)-oximinomilbemycin derivatives of formula I, to their preparation and to the use thereof for controlling pests. The invention further relates to pesticidal compositions which contain at least one of these compounds as active ingredient.

The novel compounds have the general formula I

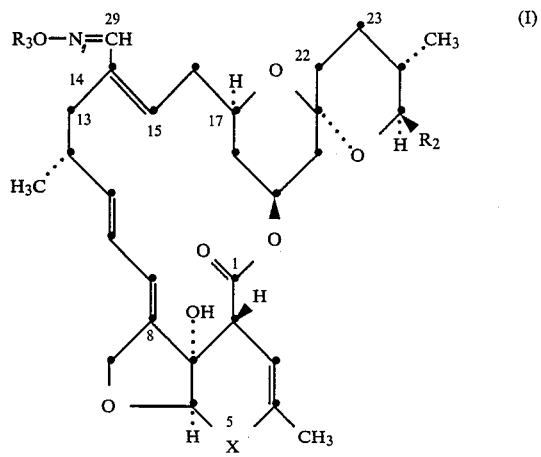

wherein
X is a group selected from —CH(OR$_1$)—, —C(O)— or —C(=N—OR)—,
R$_1$ is hydrogen or a OH protective group,
R is hydrogen, a OH protective group, an alkyl, cycloakyl or acyl group,
R$_2$ is methyl, ethyl, isopropyl, sec-butyl or the

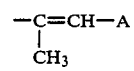

group, wherein A is methyl, ethyl or isopropyl; and
R$_3$ is hydrogen, C$_1$-C$_6$alkyl, C$_2$-C$_6$alkenyl, a radical selected from the group consisting of phenyl and benzyl which is unsubstituted or substituted by one or more members selected from the group consisting of halogen, C$_1$-C$_3$alkyl, C$_1$-C$_3$alkoxy, C$_1$-C$_3$alkylthio, C$_1$-C$_3$haloalkyl, nitro or cyano, or is the group U

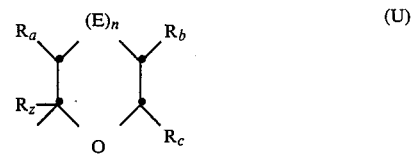

wherein n is 0, 1, 2, 3, 4 or 5, E is oxygen or —CH(R$_d$)— and R$_z$ is hydrogen, R$_a$ is hydrogen, halogen, C$_1$-C$_3$alkyl, C$_1$-C$_3$alkoxy or 2-tetrahydropyranyl, and R$_b$, R$_c$ and R$_d$ are each independently hydrogen, halogen, C$_1$-C$_3$alkyl or C$_1$-C$_3$alkoxy, which group U may also be in unsaturated form.

11 Claims, No Drawings

INSECTICIDES AND PARASITICIDES

This is a divisional of application Ser. No. 160,237 now U.S. Pat. No. 4,855,317 filed on February 25, 1988.

The present invention relates to novel C(29)-oximinomilbemycin derivatives of formula I, to their preparation and to the use thereof for controlling pests. The invention further relates to pesticidal compositions which contain at least one of these compounds as active ingredient.

The novel compounds have the general formula I

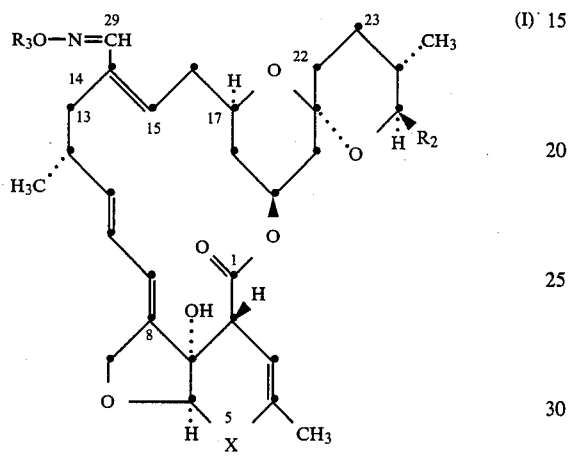

wherein
X is a group selected from —CH(OR$_1$)—, —C(O)— or —C(=N—OR)—,
R$_1$ is hydrogen or a OH protective group,
R is hydrogen, a OH protective group, an alkyl, cycloalkyl or acyl group,
R$_2$ is methyl, ethyl, isopropyl, sec-butyl or the

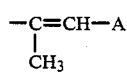

group, wherein A is methyl, ethyl or isopropyl; and
R$_3$ is hydrogen, C$_1$-C$_6$alkyl, C$_2$-C$_6$alkenyl, a radial selected from the group consisting of phenyl and benzyl which is unsubstituted or substituted by one or more members selected from the group consisting of halogen, C$_1$-C$_3$alkyl, C$_1$-C$_3$alkoxy, C$_1$-C$_3$alkylthio, C$_1$-C$_3$haloalkyl, nitro or cyano, or is the group U

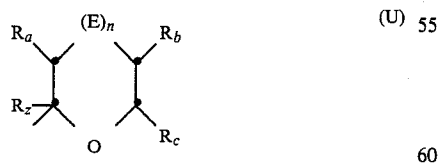

wherein n is 0, 1, 2, 3, 4 or 5, E is oxygen or —CH(R$_d$)— and R$_z$ is hydrogen, R$_a$ is hydrogen, halogen, C$_1$-C$_3$alkyl, C$_1$-C$_3$alkoxy or 2-tetrahydropyranyl, and R$_b$, R$_c$ and R$_d$ are each independently hydrogen, halogen, C$_1$-C$_3$alkyl or C$_1$-C$_3$alkoxy, which group U may also be in unsaturated form.

Preferred novel compounds are those of formula I

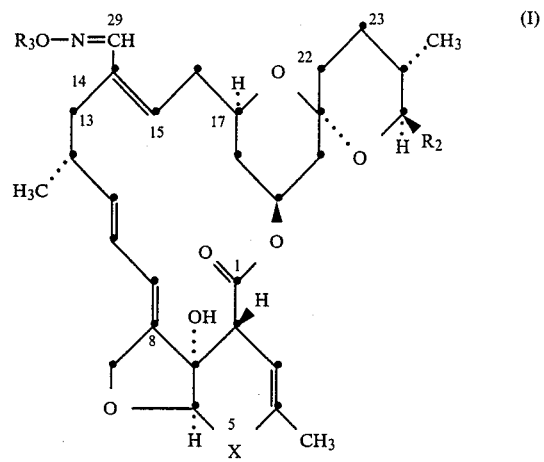

wherein
X is a group selected from —CH(OR$_1$)—, —C(O)— and —C(=N—OR)—,
R$_1$ is hydrogen or a OH protective group,
R is hydrogen, a OH protective group, or an alkyl, cycloalkyl or acyl group,
R$_2$ is methyl, ethyl, isopropyl or sec-butyl; and
R$_3$ is hydrogen, C$_1$-C$_6$alkyl, C$_2$-C$_6$alkenyl, a radical selected from the group consisting of phenyl and benzyl which is unsubstituted or substituted by one or more members selected from the group consisting of halogen, C$_1$-C$_3$alkyl, C$_1$-C$_3$alkoxy, C$_1$-C$_3$alkylthio, C$_1$-C$_3$haloalkyl, nitro or cyano, or is the group U

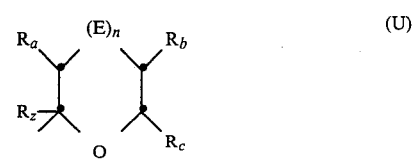

wherein n is 0, 1, 2, 3, 4 or 5, E is oxygen or —CH(R$_d$)— and R$_z$ is hydrogen, R$_a$ is hydrogen, halogen, C$_1$-C$_3$alkyl, C$_1$-C$_3$alkoxy or 2-tetrahydropyranyl, and R$_b$, R$_c$ and R$_d$ are each independently hydrogen, halogen, C$_1$-C$_3$alkyl or C$_1$-C$_3$alkoxy, which group U may also be in unsaturated form.

Particularly preferred novel compounds are those of the general formula I

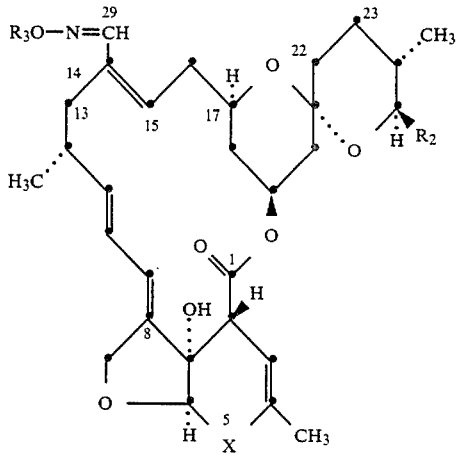

(I)

wherein
X is the —CH(OR₁)— group,
R₁ is hydrogen or a OH protective group,
R₂ is methyl, ethyl, isopropyl or sec-butyl; and
R₃ is hydrogen, $C_1$–$C_6$alkyl, $C_2$–$C_6$alkenyl, a radical selected from the group consisting of phenyl and benzyl which is unsubstituted or substituted by one or more members selected from the group consisting of halogen, $C_1$–$C_3$alkyl, $C_1$–$C_3$alkoxy, $C_1$–$C_3$alkylthio, $C_1$–$C_3$haloalkyl, nitro or cyano, or is the group U

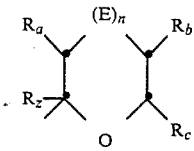

(U)

wherein n is 0, 1, 2, 3, 4 or 5, E is oxygen or —CH(R$_d$)— and R$_z$ is hydrogen, R$_a$ is hydrogen, halogen, $C_1$–$C_3$alkyl, $C_1$–$C_3$alkoxy or 2-tetrahydropyranyl, and R$_b$, R$_c$ and R$_d$ are each independently hydrogen, halogen, $C_1$–$C_3$alkyl or $C_1$–$C_3$alkoxy, which group U may also be in unsaturated form.

Preferred compounds are those wherein
n is 0 or 1,
E is oxygen, —CH(R$_x$)— or —CH(R$_x$)—CH(R$_y$)—,
R$_z$ is hydrogen,
R$_a$, R$_b$, R$_c$, R$_x$ and R$_y$ are each independently hydrogen, halogen, $C_1$–$C_3$alkyl or $C_1$–$C_3$alkoxy and R$_a$ can also be tetrahydropyranyl, or each pair of substituents R$_z$/R$_a$, R$_a$/R$_x$, R$_x$/R$_y$, R$_y$/R$_b$ and R$_b$/R$_c$ independently, as well as, if n is 0, R$_a$/R$_b$, and, if E is —CH(R$_x$)— and n is 1, R$_x$/R$_b$, can be a bond between the two adjacent carbon atoms to which said pair is attached, with the proviso that each of the substituents R$_a$, R$_x$, R$_y$, R$_b$ and R$_c$ in a single representative of the group U can belong to only one of said pairs of substituents.

Particularly preferred compounds are those wherein
n is 0 or 1,
E is oxygen, —CH(R$_x$)— or —CH(R$_x$)—CH(R$_y$)—, and
R$_a$, R$_b$, R$_c$, R$_x$, R$_y$ and R$_z$ are each hydrogen and R$_a$ can also be chlorine or tetrahydrofuranyl and R$_c$ can be bromine or the group —OCH₃, or each pair of substituents R$_z$/R$_a$ and R$_b$/R$_c$ independently of the other is a bond between the two adjacent carbon atoms to which said pair is attached.

Most preferred compounds are those wherein (i) n is 0,
R$_a$, R$_b$ and R$_z$ are hydrogen,
R$_c$ is bromine or each pair of substituents R$_z$/R$_a$ and R$_b$/R$_c$ independently of the other is a bond between the two adjacent carbon atoms to which said pair is attached;
(ii) n is 1,
E is oxygen and R$_a$, R$_b$, R$_c$ and R$_z$ are each hydrogen;
(iii) n is 1,
E is —CH(R$_x$)—,
R$_a$, R$_b$, R$_c$ and R$_z$ are each hydrogen and R$_a$ may also be chlorine or tetrahydrofuranyl and R$_c$ may be the —OCH₃ group;
(iv) n is 1,
E is —CH(R$_x$)—CH(R$_y$)—, and
R$_a$, R$_b$, R$_c$, R$_x$, R$_y$ and R$_z$ are each hydrogen.

Typical representatives of the group U are:

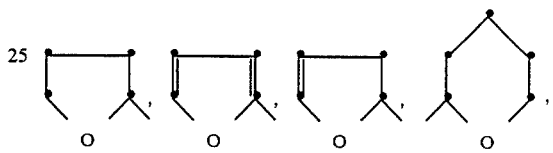

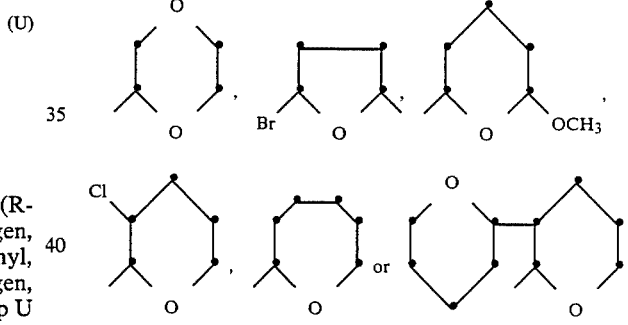

The above recitation implies no limitation.

Throughout this specification, OH protective groups R and R₁ shall in general understood as being those protective functions customarily encountered in organic chemistry. Such protective groups are, in particular, acyl and silyl groups. Examples of suitable acyl groups are the radicals R₄—C(O)—, wherein R₄ is $C_1$–$C_{10}$alkyl, $C_1$–$C_{10}$haloalkyl, or a phenyl or benzyl radical which is unsubstituted or substituted by substituents selected from the group consisting of halogen, $C_1$–$C_3$alkyl, $C_1$–$C_3$haloalkyl, $C_1$–$C_3$alkoxy, $C_1$–$C_3$haloalkoxy, cyano and/or nitro, with the preferred meanings of R₄ being $C_1$–$C_6$alkyl, $C_1$–$C_6$haloalkyl, or phenyl which is unsubstituted or substituted by halogen, $C_1$–$C_3$alkyl, CF₃ or nitro. Suitable silyl groups R₁ are the radicals —Si(R₅)(R₆)(R₇), wherein R₅, R₆ and R₇, preferably independently of one another, are $C_1$–$C_4$alkyl, benzyl or phenyl and form for example one of the groups trimethylsilyl, diphenyl-tert-butylsilyl, bis(isopropyl)methylsilyl, triphenylsilyl and the like or, preferably, tert-butyldimethylsilyl. The 5—OH group may also be in the form of benzyl ether or methoxyethoxymethyl ether, or, according to European published patent application 185,623, attached to a carbohydrate residue, hereinafter referred to for simplicity's sake as a sugar residue.

Compounds of formula I, wherein X is the —CH(OR$_1$)— or —C(=N—OR)— group and R and R$_1$ are a protective group can be converted by simple, e.g. hydrolytic, removal of the protective function into the highly active free 5-hydroxy derivatives (R$_1$; R=H) and therefore act as intermediates. However, the biological properties of these compounds are not diminished by the protective group or the sugar residue.

Preferred substituents of the phenyl groups are 1 to 3 halogen atoms, C$_1$-C$_2$alkyl, C$_1$-C$_2$alkoxy, C$_1$-C$_2$alkylthio, C$_1$-C$_2$haloalkyl or nitro or cyano and, among all radicals which contain an alkyl group, preferably those containing 1 carbon atom. These substituents, independently of one another, may be present in combination with one another.

Depending on the stated number of carbon atoms, alkyl as by itself or as moiety of a substituent will be understood as meaning for example the following groups: methyl, ethyl, propyl, butyl, pentyl, hexyl, heptyl, octyl, nonyl or decyl and the like, as well as the isomers thereof, e.g. isopropyl, isobutyl, tert-butyl, isopentyl and the like. Haloalkyl is a mono- to perhalogenated alkyl substituent, e.g. CHCl$_2$, CHF$_2$, CH$_2$Cl, CCl$_3$, CF$_3$, CH$_2$F, CH$_2$CH$_2$Cl, CHBr$_2$ etc., preferably CF$_3$. Throughout this specification, halogen will be understood as meaning fluorine, chlorine, bromine or iodine, with fluorine, chlorine or bromine being preferred. Alkenyl is an aliphatic hydrocarbon radical characterised by at least one C=C double bond, and is e.g. vinyl, 1-propenyl, allyl, 1-butenyl, 2-butenyl or 3-butenyl. Suitable cycloalkyl groups are mono- to tetracyclic groups, e.g. cyclopropyl, cyclobutyl, cyclopentyl, cyclohexyl, decalin, hydrindane, bicycloheptane, bicyclooctane, norbornane, bornane or adamantyl. These cycloaliphatic groups are preferably unsubstituted or substituted by one or more methyl groups.

The acyl and silyl groups mentioned above act not only as protective groups or hydroxyl groups present in the substituent X, but also for all other hydroxyl groups present in the compounds of this invention or in precursors thereof.

Compounds of formula I, wherein R$_1$ is hydrogen, are preferred. Acyl and silyl groups R and R$_1$ will be generally understood as meaning protective groups.

On account of their excellent activity against ectoparasites on useful animals, the 5-oximes [X=—C(=N—OR)—] constitute an important subgroup within the scope of formula I.

Throughout this specification compounds wherein R$_2$ is sec-butyl shall likewise be regarded as belonging to the class of milbemycin derivatives, although according to conventional classification they are derived from avermectin derivatives. However, avermectin aglycons (carrying an OH group in the 13α-position) can be converted into milbemycin homologues in accordance with U.S. Pat. No. 4,173,571.

Naturally occurring milbemycins (R$_1$=H; R$_2$=CH$_3$, C$_2$H$_5$ or isoC$_3$H$_7$) have solely hydrogen in 13-position. Avermectins, however, carry in 13-position an α-L-oleandrosyl-α-L-oleandrose radical which is attached through oxygen in the α-configuration to the macrolide molecule. Moreover, avermectins differ structurally from milbemycins by the presence of a 23—OH group or Δ$^{22,23}$ double bond and, usually, by the presence of a substituent R$_2$=sec-C$_4$H$_9$. Hydrolysis of the sugar residue of avermectins, readily affords the corresponding avermectinaglycons containing a 13α-hydroxy group which is adjacent to a C=C double bond. As stated above, avermectinaglycons can be converted into milbemycin homologues. In the milbemycin derivatives of the present invention, the Δ$^{22,23}$ double bond is always in hydrogenated form.

Compounds of formula I, wherein R$_2$ is the

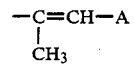

group and A is methyl, ethyl or isopropyl, represent those 23-deoxy derivatives of the naturally occurring antibiotics S541 which contain a C(29)oximino group and in 5-position contain either a free OH group, a OH protective group, a keto group or an oxime grouping.

The constitution of naturally occurring antibiotics S541 is disclosed in DE 3,532,794 and is as follows:

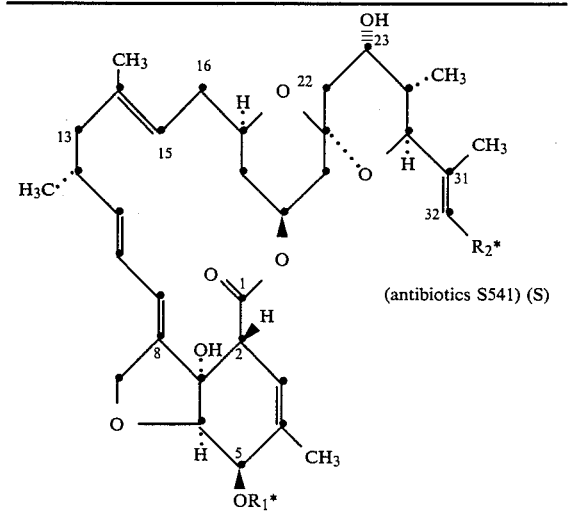

(antibiotics S541) (S)

| | | |
|---|---|---|
| factor A | R$_2$* = isoC$_3$H$_7$ | R$_1$* = H |
| factor B | R$_2$* = CH$_3$ | R$_1$* = CH$_3$ |
| factor C | R$_2$* = CH$_3$ | R$_1$* = H |
| factor D | R$_2$* = C$_2$H$_5$ | R$_1$* = H |
| factor E | R$_2$* = C$_2$H$_5$ | R$_1$* = CH$_3$ |
| factor F | R$_2$* = isoC$_3$H$_7$ | R$_1$* = CH$_3$ |

On account of their pronounced parasiticidal and insecticidal activity, the following subgroups of compounds of formula I are especially preferred:

Group Ia: Compounds of formula I, wherein X is a group selected from —CH(OR$_1$)—, —C(O)— or —C(=N—OH)—, in which R$_1$ is hydrogen, R$_4$—C(O)— or —Si(R$_5$)(R$_6$)(R$_7$), wherein R$_4$ is C$_1$-C$_{10}$alkyl, C$_1$-C$_{10}$haloalkyl or a member selected from the group consisting of phenyl and benzyl which is unsubstituted or substituted by halogen, C$_1$-C$_3$alkyl, C$_1$-C$_3$haloalkyl, C$_1$-C$_3$alkoxy, C$_1$-C$_3$haloalkoxy, cyano and/or nitro; R$_5$, R$_6$ and R$_7$ are each independently C$_1$-C$_4$alkyl, benzyl or phenyl; R$_2$ is methyl, ethyl, isopropyl, sec-butyl or the group

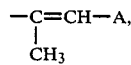

wherein A is methyl, ethyl or isopropyl; and R$_3$ is hydrogen, C$_1$-C$_4$alkyl, a radical selected from the group consisting of phenyl and benzyl which is unsubstituted or substituted by one or more members of the group consisting of halogen, $C_1$-$C_2$alkyl, $C_1$-$C_2$alkoxy, $C_1$-$C_2$alkylthio, $C_1$-$C_2$haloalkyl, nitro or cyano, or is the group U

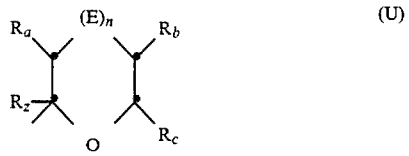

wherein n is 0 or 1, E is oxygen or $CH_2$ and $R_z$ is hydrogen, $R_a$ is hydrogen, fluorine, chlorine, bromine, methyl or 2-tetrahydropyranyl, and $R_b$ and $R_c$ are each independently of the other hydrogen or methyl.

Group Ib: Compounds of formula I, wherein X is a group selected from —CH(OR$_1$)—, —C(O)— or —C(=N—OH)—, in which $R_1$ is hydrogen, $R_4$—C(O)— or —Si($R_5$)($R_6$)($R_7$), wherein $R_4$ is $C_1$-$C_{10}$alkyl, $C_1$-$C_{10}$haloalkyl or a member selected from the group consisting of phenyl and benzyl which is unsubstituted or substituted by halogen, $C_1$-$C_3$alkyl, $C_1$-$C_3$haloalkyl, $C_1$-$C_3$alkoxy, $C_1$-$C_3$haloalkoxy, cyano and/or nitro; $R_5$, $R_6$ and $R_7$ are each independently $C_1$-$C_4$alkyl, benzyl or phenyl; $R_2$ is methyl, ethyl, isopropyl or sec-butyl; and $R_3$ is hydrogen, $C_1$-$C_4$alkyl, a radical selected from the group consisting of phenyl or benzyl which is unsubstituted or substituted by one to three members selected from the group consisting of halogen, $C_1$-$C_2$alkyl, $C_1$-$C_2$alkoxy, $C_1$-$C_2$alkylthio, $C_1$-$C_2$haloalkyl, nitro or cyano, or is the group U

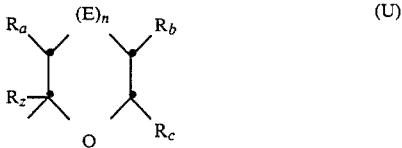

wherein n is 0 or 1, E is oxygen or $CH_2$ and $R_z$ is hydrogen, $R_a$ is hydrogen, fluorine, chlorine, bromine, methyl or tetrahydropyranyl, and $R_b$ and $R_a$ are each independently of the other hydrogen, halogen or methyl.

Group Ic: Compounds of formula I, wherein X is the —CH(OR$_1$)— group, in which $R_1$ is hydrogen, $R_4$—C(O)— or —Si($R_5$)($R_6$)($R_7$), wherein $R_4$ is $C_1$-$C_{10}$alkyl, $C_1$-$C_{10}$haloalkyl or a member selected from the group consisting of phenyl and benzyl which is unsubstituted or substituted by halogen, $C_1$-$C_3$alkyl, $C_1$-$C_3$haloalkyl, $C_1$-$C_3$alkoxy, $C_1$-$C_3$haloalkoxy, cyano and/or nitro; $R_5$, $R_6$ and $R_7$ are each independently $C_1$-$C_4$alkyl, benzyl or phenyl; $R_2$ is methyl, ethyl, isopropyl or sec-butyl; and $R_3$ is hydrogen, $C_1$-$C_4$alkyl, a radical selected from the group consisting of phenyl or benzyl which is unsubstituted or substituted by one to three members selected from the group consisting of halogen, $C_1$-$C_2$alkyl, $C_1$-$C_2$alkoxy, $C_1$-$C_2$alkylthio, $C_1$-$C_2$haloalkyl, nitro or cyano, or is the group U

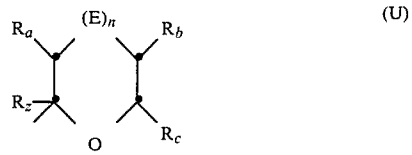

wherein n is 0 or 1, E is oxygen or $CH_2$ and $R_z$ is hydrogen, $R_a$ is hydrogen, fluorine, chlorine, bromine, methyl or tetrahydropyranyl, and $R_b$ and $R_a$ are each independently of the other hydrogen, halogen or methyl.

Group Id: Compounds of formula I, wherein $R_1$ is hydrogen, $R_2$ is methyl, ethyl, isopropyl or sec-butyl, and $R_3$ is hydrogen, $C_1$-$C_4$alkyl, phenyl, benzyl, or a group selected from

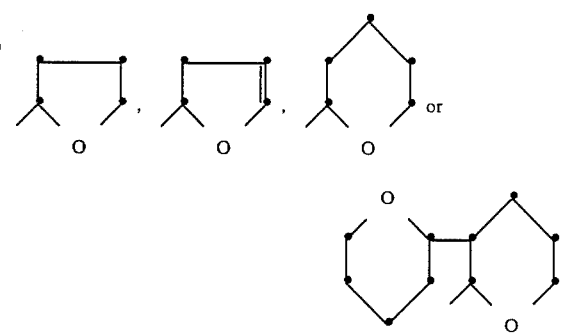

Group Ie: Compounds of formula I, wherein X is a group —C(O) or C(=N—OH), $R_2$ is methyl, ethyl, isopropyl or sec-butyl, and $R_3$ is hydrogen, $C_1$-$C_4$alkyl, phenyl, benzyl, or a group selected from

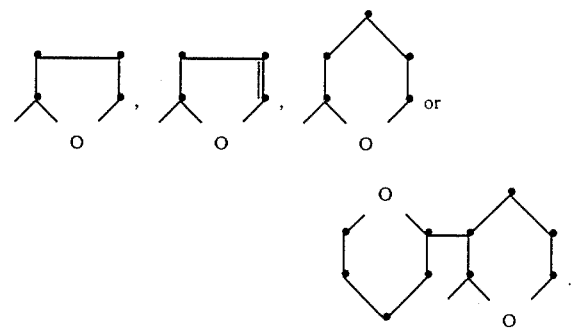

Group If: Compounds of formula I, wherein $R_1$ is hydrogen, $R_2$ is methyl, ethyl, isopropyl, or sec-butyl, and $R_3$ is hydrogen or $C_1$-$C_3$alkyl.

Compounds of formula I, wherein $R_2$ is methyl, are preferred. Particularly preferred compounds, however, are those representatives of formula I, wherein $R_2$ is ethyl.

Particularly preferred representatives of formula I are:
5-acetoxy-29-methoximinomilbemycin D,
5-(dimethyl-tert-butylsilyloxi)-29-hydroximinomilbemycin $A_4$,
29-hydroximinomilbemycin $A_4$,
29-methoximinomilbemycin $A_4$,
29-phenoximinomilbemycin $A_4$,
29-(tetrahydropyran-2-yl)-oximinomilbemycin $A_4$
5,29-bis(hydroximino)milbemycin $A_4$ The compounds of formula I are prepared by reacting a 29-oxo-milbemycin of formula II

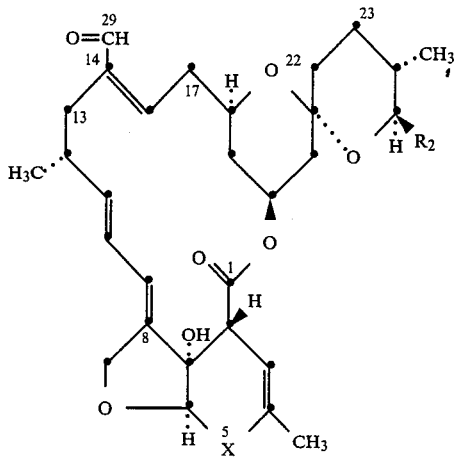

with a primary oxamine of formula III

  (III)

or a salt thereof and, if desired, further reacting the resultant compound of formula I, if $R_3$ is hydrogen, with a halide of formula IV

  (IV)

in which formulae above the substituents $R_2$ and $R_3$ are as defined for formula I, X is $-C(OR_1)-$, wherein $R_1$ is hydrogen or a OH protective group, and Hal is halogen, and $R_3'$ has all the meanings of $R_3$ except hydrogen, such that a start is usually made from compounds of formula II which contain either a free 5-hydroxy group and, if desired, the products obtained are subsequently acylated or silylated at the 5-0 atom, or a start is made from a compound of formula II which is already silylated or acylated in 5-position and, if desired, the protective group is removed or, if it is desired to prepare compounds of formula I, wherein X is the $-C(O)-$ group, a start is made from compounds of formula II which contain a free 5-hydroxy group and said compounds are treated with a suitable oxidising agent; or, if it is desired to prepare compounds of formula I, wherein X is the $-C(=N-OR)-$ group, in which R is as defined for formula I, a start is made from a compound of formula I, wherein X is $-C(O)-$, which is reacted with hydroxylamine or a salt thereof and, if desired, the substituent R is subsequently introduced, or the reaction is carried out with a compound of formula $NH_2-OR$ or salt thereof. Hal in formula IV is preferably chlorine or bromine.

The C(29)-oximes of formula I are prepared by reacting a C(29)-oxo compound of formula II with a primary oxamine of formula III or a salt thereof, preferably a mineral acid salt thereof, most preferably the hydrochloride thereof. The reaction is conveniently carried out in a suitable solvent, e.g. a lower alkanol, e.g. methanol, ethanol or propanol; an ethereal compound such as tetrahydrofuran or dioxan; an aliphatic carboxylic acid such as acetic acid or propionic acid; water or in mixtures of these solvents with one another or with other customary inert solvents. The reaction temperatures can vary within wide ranges. The process is conveniently carried out, for example, in the temperature range from $+10°$ to $+100°$ C. If the oxamine is used in the form of a salt, e.g. as hydrochloride, then to neutralise the acid (e.g. HCl) it is convenient to add a base conventionally employed for this purpose and then to carry out the reaction in the presence of a hydrophilic agent, e.g. a molecular sieve. Suitable bases are organic and inorganic bases, e.g. tertiary amines such as trialkylamines (trimethylamine, trimethylamine, tripropylamine etc.), pyridine and pyridine bases (4-dimethylaminopyridine, 4-prrolidylaminopyridine etc.), oxides, hydrides and hydroxides, carbonates and bicarbonates of alkali metals and alkaline earth metals (CaO, BaO, NaOH, KOH, NaH, $Ca(OH)_2$, $KHCO_3$, $NaHCO_3$, $Ca(HCO_3)_2$, $K_2CO_3$, $Na_2CO_3$), as well as alkali metal acetates such as $CH_3COONa$ or $CH_3COOK$. Suitable bases are also alkali metal alcoholates such as $C_2H_5ONa$, $n-C_3H_7ONa$ etc. Trialkylamines are preferred, especially triethylamine.

The reaction of an oxime of formula I, wherein $R_3$ is hydrogen, with a halide of formula IV is normally carried out in an inert solvent or in one of the reactants, provided these are liquid. Examples of suitable solvents are: ethers and ethereal compounds such as dialkyl ethers (diethyl ether, diisopropyl ether, tert-butylmethyl ether, dimethoxyethane, dioxan, tetrahydrofuran, anisole etc.); halogenated hydrocarbons such as chlorobenzene, methylene chloride, ethylene chloride, chloroform, carbon tetrachloride or tetrachloroethylene etc.; or sulfoxides such as dimethylsulfoxide, in which case aromatic or aliphatic hydrocarbons such as benzene, toluene, xylene, petroleum ether, ligroin, cyclohexane etc. may also be present. In some cases it can be advantageous to carry out the reactions in an inert gas atmosphere (e.g. argon, helium, nitrogen etc.) and/or in absolute solvents. If desired, the final products can be purified in conventional manner, for example by washing, dispersing, extraction, recrystallisation, chromatography and the like.

The reaction of a compound of formula I, wherein $R_3$ is hydrogen, with a halide of formula IV is normally carried out in one of the above mentioned inert solvents, usually in the temperature range from $0°$ to $+100°$ C., preferably from $20°$ to $60°$ C. To neutralise the acids formed as by-products it is convenient to carry out the reaction in the presence of neutralising agent. Suitable neutralising agents are organic bases, for example tertiary amines such as trialkylamines (trimethylamine, triethylamine, diisopropylmethylamine, tripropylamine etc.), pyridine and pyridine bases (4-dimethylaminopyridine, 4-pyrrolidylaminopyridine etc.). Pyridine is preferred. The neutralising agent is normally employed in at least equimolar amount, based on the starting materials. The organic base can also be used as solvent. A catalyst such as p-dimethylaminopyridine can also be added.

The oxime derivatives of formula III and the halides of formula IV are generally known or can be prepared by methods analogous to those employed for preparing the known representatives.

To prepare the 5-oximes [$X=-C(=N-OR)-$] within the scope of formula I it is possible to remove the substituents present at the 5-C atom and, if desired, to replace them by other substituents provided these conform to the definitions as given in this specification. The removal and introduction of substituents as defined herein can be effected by methods which are known per se. Acyl and silyl groups are introduced by starting conveniently from compounds of formula I, wherein X is —CH(OH)— or —C(=N—OH)—, from compounds of formula (S), in which R₁ is hydrogen, or from compounds of formula VIII. Compounds of formula I, wherein X is —C(=N—OR)—, can be prepared for example by reacting compounds of formula I, in which X is —C(O)—, with hydroxylamine or a salt thereof and, if desired, subsequently introducing the substituent R, where R is as defined for formula I but is not hydrogen, or by carrying out the reaction with a compound of formula NH₂—OR, wherein R is as defined for formula I but is not hydrogen, or a salt thereof. Examples of suitable salts are those of the aforementioned amino compounds with sulfuric acid, nitric acid and, preferably, hydrochloric acid. The reaction is conveniently caried out in a suitable solvent, e.g. a lower alkanol such as methanol, ethanol or propanol; an ethereal compound such as tetrahydrofuran or dioxan, an aliphatic carboxylic acid such as acetic acid or propionic acid; water or in mixtures of these solvents with one another or with other customary inert solvents. The reaction temperatures may vary within wide ranges. It is convenient to carry out the reaction in the range from about +10° to +100° C. If hydroxylamine is employed in the form of one of its salts, e.g. in the form of its hydrochloride, then in order to neutralise the acid it is advantageous to add a base customarily employed for such purposes and to perform the reaction in the presence of a hydrophilic agent, e.g. a molecular sieve. Suitable bases are both organic and inorganic bases, e.g. tertiary amines such as trialkylamines (trimethylamine, triethylamine, tripropylamine and the like), pyridine and pyridine bases (4-dimethylaminopyridine, 4-pyrrolidylaminopyridine and the like), oxides, hydrides and hydroxides, carbonates and bicarbonates of alkali metals and alkaline earth metals (CaO, BaO, NaOH, KOH, NaH, Ca(OH)₂, KHCO₃, NaHCO₃, Ca(HCO₃)₂, K₂CO₃, Na₂CO₃), as well as alkali metal acetates such as CH₃COONa or CH₃COOK. Alkali metal alcoholates such as C₂H₅ONa and C₃H₇-nONa are also suitable bases. Triethylamine is preferred.

The 5-ketomilbemycins falling within the scope of formula I, wherein X is —C(O)—, can be prepared, for example, by treating compounds of formula I, in which X is —CH(OH)—, with a suitable oxidising agent. Examples of suitable oxidising agents are activated manganese dioxide, oxalyl chloride/dimethylsulfoxide/triethylamine or chromium trioxide/pyridine. A suitable process is the Oppenauer oxidation, in which compounds of formula I, wherein X is —CH(OH)—, are reacted with a ketone, preferably cyclohexanone or acetone, in the presence of an aluminium alcoholate, preferably aluminium isopropylate or aluminium tert-butylate.

The oxidation is preferably carried out in an inert solvent. Suitable solvents are alkanes such as hexane, heptane or octane, aromatic hydrocarbons such as benzene, toluene or xylenes, or, preferably, chlorinated hydrocarbons, in particular methylene chloride. The oxidation is conveniently carried out in the temperature range from −80° to +60° C., preferably from −60° to +30° C.

Those compounds in which X is the —CHOH— group can obtained again by reduction in a manner known per se from compounds of formula I, wherein X is the —C(O)— group. The reduction can be carried out by catalytic hydrogenation with a platinum or Raney nickel catalyst or by the Meerwein/Ponndorf/Verley reduction with aluminium isopropylate in isopropanol.

The compounds of formula II can be obtained by an oxidative allylic rearrangement from 15-hydroxymilbemycin derivatives of formula V

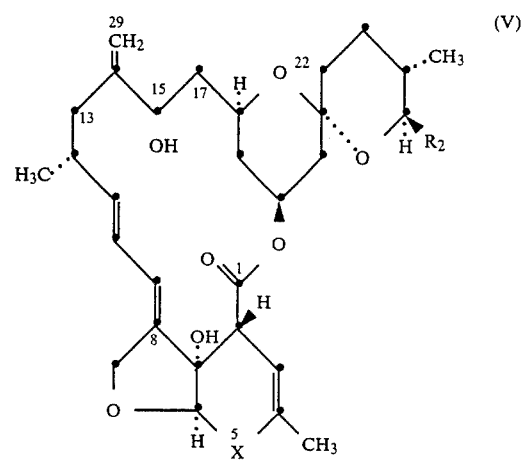

wherein X and R₂ are as defined for formula I.
The reaction can be illustrated as follows:
Oxidative allylic rearrangement

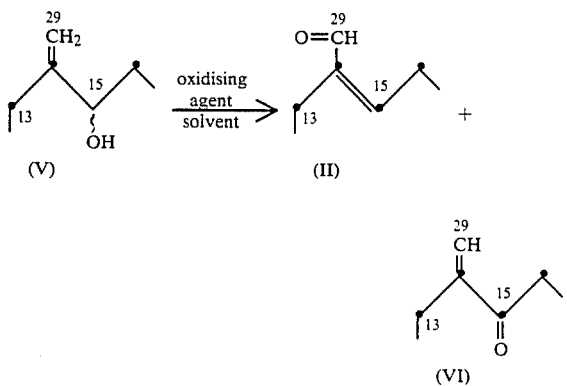

of the allyl alcohol of formula (V) to give a 29-oxo compound of formula (II). In this reaction, the allyl alcohol of formula (V) is rearranged by oxidation with a suitable oxidising agent in an inert solvent to give the corresponding aldehyde (=29-oxo compound) of formula II. In general, the corresponding unsaturated ketone of formula VI is formed as by-product in the course of the reaction. This by-product is itself an intermediate as, on account of its reactivity, it can be employed for the synthesis of further milbemycin derivatives. Normally the trans- and cis-forms of the aldehyde of formula II are formed side by side, with the trans-form generally predominating. The compounds of formula II and VI can be readily separated from each other by column chromatography, for example over silica gel.

The 29-oxo compounds of formula II have the following chemical structure

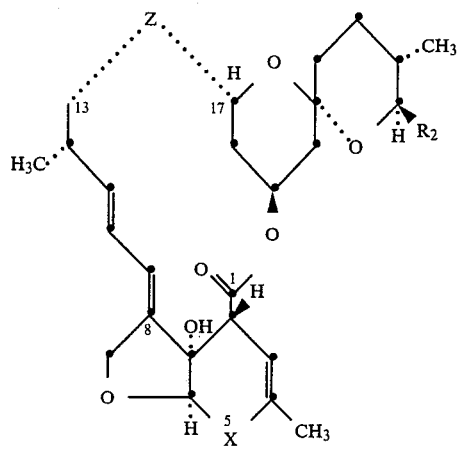

wherein Z is a group

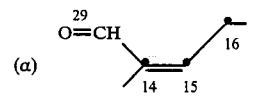

$$\left[ = \Delta^{14,15\text{-}trans}\text{-29-oxo compounds of formula X} \right]$$

or

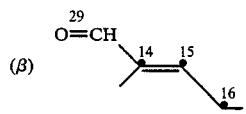

$$\left[ = \Delta^{14,15\text{-}cis}\text{-29-oxo compounds of formula X} \right]$$

and X and $R_2$ are as defined for formula I. The conversion of the $\Delta^{14,15\text{-}trans}$-29-oxo compounds of formula X into the $\Delta^{14,15\text{-}cis}$-29-oxo compound of formula X can be effected by methods analogous to per se known processes. Owing to their specific structure, compounds of formula X are predestined for the preparation of the valuable final products of formula I, as they are the direct precursors for the preparation thereof.

Suitable reagents for the (oxidative) rearrangement are, in particular, chromium(VI) compounds, e.g. pyridinium chromate, pyridinium chlorochromate and the like. It is convenient to carry out the reaction in an inert solvent. Examples of suitable solvents are ethers and ethereal compounds such as dialkyl ethers (diethyl ether, diisopropyl ether, tert-butylmethyl ether, dimethoxyethane), dioxane, tetrahydrofuran, anisole and the like; halogenated hydrocarbons such as chlorobenzene, methylene chloride, ethylene chloride, chloroform, carbon tetrachloride, tetrachloroethylene and the like; sulfoxides such as dimethyl sulfoxide; amides such as N,N-dimethylformamide; esters such as ethyl acetate, propyl acetate, butyl acetate and the like; as well as mixtures of these solvents with one another or with water and/or other customary inert solvents such as benzene, xylene, petroleum ether, ligroin, cycohexane and the like. In some cases, it may prove advantageous to perform the reaction or partial steps thereof under an inert gas atmosphere (e.g. argon, helium, nitrogen and the like) and/or in absolute solvents. If desired, intermediates can be isolated from the reaction medium and, if required, purifed in conventional manner before further reaction, e.g. by washing, dispersing, extraction, recrystallisation, chromatography etc. However, it is possible to dispense with such intermediary purification steps, i.e. by only purifying the corresponding final products. The reaction temperature for the oxidative allylic rearrangement is normally in the range from $-50°$ to $+50°$ C., preferably from $-10°$ to $+30°$ C. The reaction time depends essentially on the reaction temperatures and varies in general from 10 minutes to about 12 hours.

Owing to their structure, the ketones of formula VI

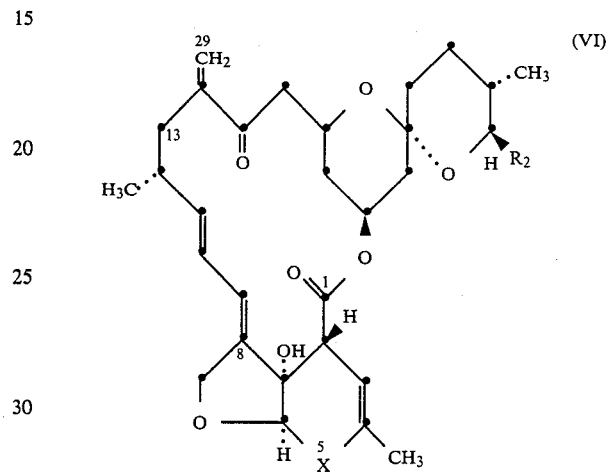

wherein X and $R_2$ are as defined for formula I, are suitable intermediates for the preparation of further milbemycin derivatives.

Compounds of formula II can also be obtained by an allylic rearrangement of a compound of formula A

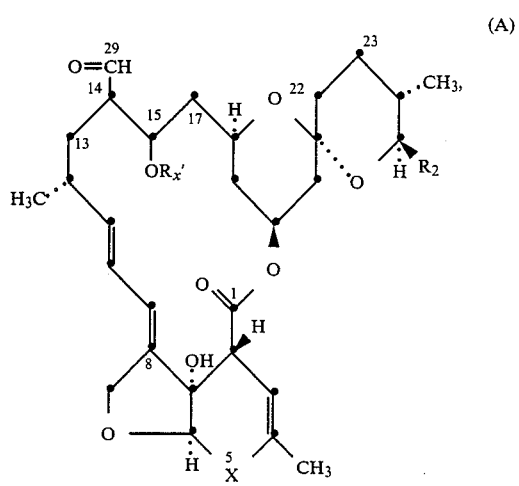

wherein X and $R_2$ have one of the meanings given for formula I and $R_x'$ is hydrogen or an easily removable group, by generally known methods, for example by treatment with an aqueous acid (e.g. a mineral acid such as HCl, HBr, $H_2SO_4$ etc., an organic acid such as p-toluenesulfonic acid, camphorsulfonic acid etc.), with or without the addition of a customary inert solvent such as tetrahydrofuran, diethyl ether, dioxan and the like, to give a compound of formula B

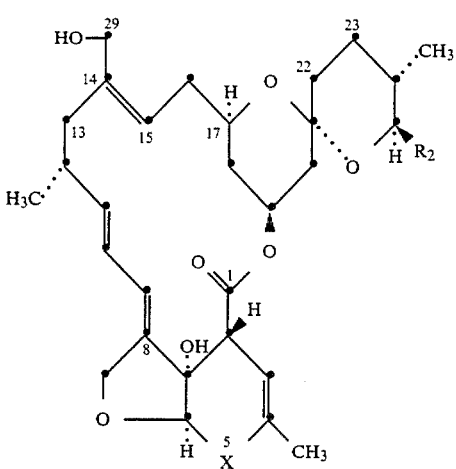

(B)

wherein X and $R_2$ are as defined for formula I, and converting the resultant compound of formula B by methods known per se, e.g. by oxidation with a suitable reagent, to give a compound of formula II.

A suitable reagent for the oxidation is e.g. activated manganese dioxide, oxalyl chloride/dimethyl sulfoxide/triethylamine, chromium trioxide/pyridine or other oxidising agents known to the skilled person. The oxidation is normally carried out in an inert solvent.

Suitable solvents are hydrocarbons such as hexane, heptane, octane, aromatic hydrocarbons such as benzene, toluene, xylenes and, preferably, chlorinated hydrocarbons, preferably methylene chloride. The reactions are carried out in the temperature range from −80° to +60° C., preferably from −60° to +30° C.

The starting compounds of formula V can be obtained by singulett oxygen oxidation from suitably modified milbemycin derivatives of formula VII

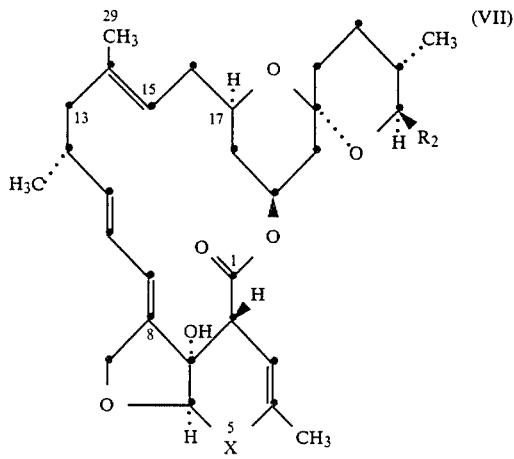

(VII)

wherein X and $R_2$ are as defined for formula I, and subsequent selective reduction of the 15-peroxide obtained as intermediate

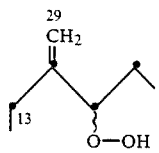

15-peroxide with sodium borohydride, lithium aluminium hydride or triphenylphosphine. The reaction is carried out in visible light in the presence of a sensitiser, under normal pressure and in the temperature range from −90° C. to +45° C., preferably from 0° to +20° C., in an inert solvent. It is preferred to carry out the reaction in an irradiating apparatus.

The reaction course can be illustrated as follows:

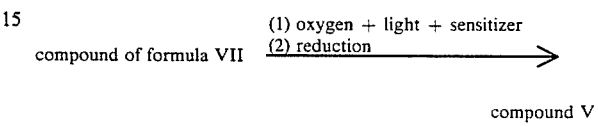

(q.v. H. H. Wassermann et al, "Singulett Oxygen", Academic Press, New York 1979; or B. Ranby et al., "Singulett Oxygen Reactions with Organic Compounds and Polymers", Wiley, New York 1978).

Compounds of formula II can be produced by methods analogous to the above described process.

Examples of suitable solvents are ethers and ethereal compounds such as diethyl ether, diisopropyl ether, dioxane and tetrahydrofuran; aromatic hydrocarbons such as benzene, toluene and xylenes; ketones such as acetone, methyl ethyl ketone and cyclohexanone; nitriles such as acetonitrile; esters such as ethyl acetate and butyl acetate; and dimethylformamide, dimethyl sulfoxide and halogenated hydrocarbons; or mixtures of these solvents with water.

Suitable sensitisers are dyes such as methylene blue, Bengal pink, chlorophyll, erysathrosin, eosine, zinc tetraphenyl porphine, hematoporphyrin, riboflavine, fluorescein or acridine orange. Selective reduction is carried out in the temperature range from 0° to 20° C., without further working up, upon conclusion of the oxidation.

As light source it is convenient to use a lamp having a strength of 60 to 500 watt, preferably of 100 to 350 watt. If it is desired to protect the 5-hydroxy group, then suitable protective groups are the silyl and acyl groups mentioned for $R_1$ or e.g. a benzyl ether, methoxyethoxymethyl ether, or dihydrofuran or dihydropyran radicals. These protective groups can be introduced into compounds of formula VII and later removed again in conventional manner.

The compounds of formula VII wherein X is the —CH(OR$_1$)— group, $R_1$ is hydrogen, and $R_2$ is methyl, ethyl, isopropyl or sec-butyl, have either become known from U.S. Pat. No. 3,950,360 and were originally designated as "Antibiotics B-41-A", later called "milbemycin A" compounds, or they are known from U.S. Pat. No. 4,346,171 and are designated as "B-41" or "milbemycin D", or they have become known from U.S. Pat. No. 4,173,571 and are designated as 13-deoxy-22,23-dihydroavermectins ($R_2$=sec-butyl). The known naturally occurring milbemycins have the following chemical structure [formula (VIII)]:

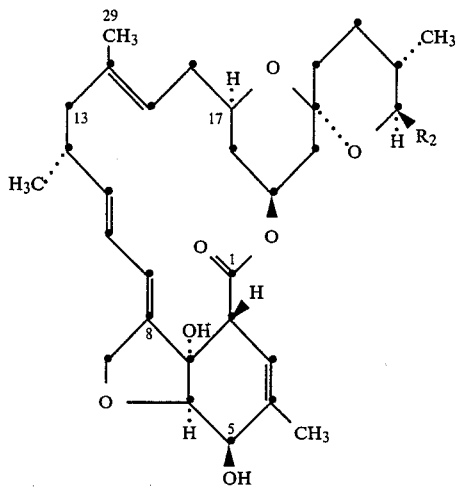

(VIII)

| | |
|---|---|
| R$_2$ = CH$_3$ | milbemycin A$_3$ |
| R$_2$ = C$_2$H$_5$ | milbemycin A$_4$ |
| R$_2$ = isoC$_3$H$_7$ | milbemycin D |
| R$_2$ = sec-C$_4$H$_9$ | 13-deoxy-22,23-dihydro-C-076-B1a-aglycon or 13-deoxy-22,23-dihydroavermectin-B1a-aglycon. |

Compounds of formula VII, wherein X is the —CH(OR$_1$)— group, in which R$_1$ is hydrogen and R$_2$ is the

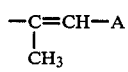

group, wherein A is as defined for formula I, are C(23)deoxy derivatives of the known naturally occurring antibiotics S541 which are known from DE No. 3,532,794 and are characterised by the following chemical structure:

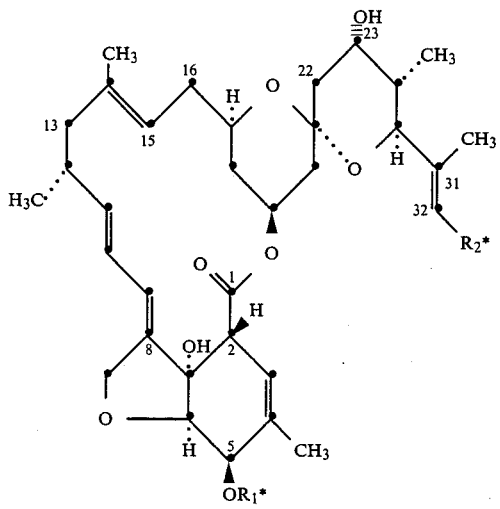

(antibiotics S541)(S)

| | | |
|---|---|---|
| factor A | R$_2$* = isoC$_3$H$_7$ | R$_1$* = H |
| factor B | R$_2$* = CH$_3$ | R$_1$* = CH$_3$ |
| factor C | R$_2$* = CH$_3$ | R$_1$* = H |
| factor D | R$_2$* = C$_2$H$_5$ | R$_1$* = H |
| factor E | R$_2$* = C$_2$H$_5$ | R$_1$* = CH$_3$ |
| factor F | R$_2$* = isoC$_3$H$_7$ | R$_1$* = CH$_3$ |

The hydroxy group in C(23)-position in the antibiotics S541 can be removed by a method analogous to that described in U.S. Pat. No. 4,328,335, and the antibiotics S541 can thus be converted into the corresponding 23-deoxy derivatives. For this conversion it is necessary first to protect selectively those compounds having a free 5-hydroxy group (R$_1$*=H) by reaction with one of the aforementioned silylating reagents Y-Si(R$_5$)(R$_6$)(R$_7$) or with tert-butyldimethylsilyloxyacetyl chloride. The reaction of these protected compounds, in which R$_1$* is replaced by Si(R$_5$)(R$_6$)(R$_7$) or C(=O)CH$_2$OSi(CH$_3$)$_2$t—C$_4$H$_9$ and the 23-C-atom is substituted by OH, with p-methylphenylchlorothionoformate gives derivatives of antibiotics S541 which are substituted in 23-position by —O—C(=S)—O—(4—CH$_3$—C$_6$H$_4$). These 23-O-(4-methylphenoxy)thiocarbonyl derivatives of antibiotics S541 are then used as starting meterials for the reduction with tributyltin hydride, in toluene and in the presence of azobisisobutyronitrile at 80°-120° C., to give the corresponding 23-deoxy derivatives (position 23 unsubstituted).

All those derivatives of formulae I and VII wherein R$_1$ has a meaning other than hydrogen (R$_1$*=OH protective group), are prepared by acylating or silylating the 5-OH group, as well as, if desired, starting materials such as milbemycins or S541 antibiotics or intermediates in which it is desired to protect the hydroxyl group in 5-position. The introduction of the acyl group is usually effected with the corresponding acyl halides or acyl anhydrides, preferably to introduce the initially defined R$_4$C(O)-group. For the silylation it is convenient to use a silane of the formula Y-Si(R$_5$)(R$_6$)(R$_7$), wherein each of R$_5$, R$_6$ and R$_7$ is one of the radicals indicated above. The term acyl halide denotes acyl chloride or acyl bromide and Y is a silyl leaving group. Examples of silyl leaving groups Y are bromide, chloride, cyanide, azide, acetamide, trifluoroacetate or trifluoromethanesulfonate. This recitation constitutes no limitation; further typical silyl leaving groups are known to the skilled person.

5-O-Acylations and 5-O-silylations are carried out in anhydrous medium, preferably in inert solvents and, most preferably, in aprotic solvents. The reaction conveniently takes place in the temperature range from 0° to 80° C., preferably from 10° to 40° C. It is preferred to add an organic base. Examples of suitable bases are tertiary amines such as triethylamine, triethylenediamine, triazole and, preferably, pyridine, imidazole or 1,8-diazabicyclo[5.4.0]-undec-7-ene (DBU).

The removal of these silyl and acyl radicals R$_1$ and R$_1$* in 5-position is effected by selective mild hydrolysis (→R$_1$; R$_1$*=H), for example with arylsulfonic acid in alcoholic solution or by another method known to the skilled person.

Acyl radicals are also preferably removed under basic conditions (e.g. in an alcoholic ammonium solution).

The described process for the preparation of compounds of formula I constitutes in all its partial steps an object of the present invention.

The compounds of formula I are most suitable for controlling pests of animals and plants in all their development stages, including in particular ectoparasites of animals. These last mentioned pests comprise those of the order Acarina, in particular pests of the families Ixodidae, Dermanyssidae, Sarcoptidae, Psoroptidae; of the orders Mallophaga, Siphonaptera, Anoplura (e.g. family of the Haematopinidae); and of the order Diptera, in particular pests of the families Muscidae, Calliphoridae, Oestridae, Tabanidae, Hippoboscidae, and Gastrophilidae.

The compounds of formula I can also be used to combat hygiene pests, especially those of the order Diptera (families Sarcophagidae, Anophilidae and Culicidae); of the order Orthoptera, of the order Dictyoptera (e.g. family of the Blattidaé), and of the order Hymenoptera (e.g. family of the Formicidae).

The compounds of formula I also have a lasting action against mites and insects which are parasites of plants. When used to control spider mites of the order Acarina, they are effective against eggs, nymphs and adults of Tetranychidae (Tetranychus spp. and Panonychus spp.). They also have excellent activity against sucking insects of the order Homoptera, in particular against pests of the families Aphididae, Delphacidae, Cicadellidae, Psyllidae, Coccidae, Diaspididae and Eriophydidae (e.g. the rust mite on citrus fruit); of the orders Hemiptera, Heteroptera and Thysanoptera; and against plant-feeding insects of the orders Lepidoptera, Coleoptera, Diptera and Orthoptera.

The compounds of formula I are also suitable for use as soil insecticides for controlling pests in the soil.

The compounds of formula I are therefore effective against all development stages of sucking and feeding insects in crops such as cereals, cotton, rice, maize, soybeans, potatoes, vegetables, fruit, tobacco, hops, citrus fruit, avocados and others.

The compounds of formula I are also effective against plant nematodes of the genera Meloidogyne, Heterodera, Pratylenchus, Ditylenchus, Radopholus, Rhizoglyphus and others.

Further, compounds of formula I act against helminths in all development stages, among which the endoparasitic nematodes can be the cause of severe diseases in mammals and fowl, for example in sheep, pigs, goats, cattle, horses, donkeys, dogs, cats, guinea pigs, cage-birds. Typical nematodes having this indication are: Haemonchus, Trichostrongylus, Ostertagia, Nematodirus, Cooperia, Ascaris, Bunostomum, Oesphagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris and Parascaris. The particular advantage of the compounds of formula I is their effectiveness against those parasites that are resistant to benzimidazole-based parasiticides.

Certain species of the genera Nematodirus, Cooperia and Oesophagostomum attack the intestinal tract of the host animal, whereas others of the genera Haemonchus and Ostertagia parasiticise in the stomach and those of the genus Dictyocaulus in the lung tissue. Parasites of the families Filariidae and Setariidae are found in internal cell tissue and internal organs, e.g. in the heart, blood vessels, lymph vessels and in subcutaneous tissue. In this connection, particular mention is to be made of the dog heartworm, *Dirofilaria immitis*. The compounds of formula I are highly effective against these parasites.

The compounds of formula I are also suitable for controlling pathogenic parasites in humans, among which parasites there may be mentioned as typical representatives occurring in the alimentary tract those of the genera Ancylostoma, Necator, Ascaris, Strongyloides, Trichinella, Capillaria, Trichuris and Enterobius. The compounds of this invention are also effective against parasites of the genera Wuchereria, Brugia, Onchocerca and Loa of the family of the Filariidae which occur in the blood, in tissue and various organs, and, in addition, against Dracunculus and parasites of the genera Strongyloides and Trichinella which infest in particular the gastro-intestinal tract.

The compounds of formula I are used in unmodified form or, preferably, together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the nature of the compositions, the methods of application such as spraying, atomising, dusting, scattering or pouring, are chosen in accordance with the intended objectives and the prevailing circumstances.

The compounds of formula I are administered to warm-blooded animals at rates of application of 0.01 to 10 mg/kg of body weight. If the compounds of formula I, or compositions containing them, are used for controlling endoparasitic nematodes, cestodes and trematodes in domestic animals and productive livestock, for example cattle, sheep, goats, cats and dogs, they can be administered to the animals in both single and repeated doses. Depending on the species of animal, the individual doses are preferably administered in amounts ranging from 0.1 to 10 mg/kg of body weight. A better action is often achieved by protracted administration, or lower total doses will also suffice. The compounds, or compositions containing them, can also be added to feeds and drinks. The ready-prepared feeds contain the active ingredients preferably in a concentration of 0.005 to 0.1 percent by weight. The compositions can be administered to the animals perorally in the form of solutions, emulsions, suspensions, powders, tablets, pellets, boluses or capsules.

If the physical and toxicological properties of solutions or emulsions permit it, the compounds of formula I, or compositions containing them, can also be injected into animals for example subcutaneously, administered intraruminally or applied to the bodies of the animals by the pour-on method. Administration by means of salt licks or molasses blocks is also possible. The compounds of formula I are applied to enclosed crop areas in amounts of 10 g to 1000 g per hectare. They are also used in pens, livestock buildings or other buildings.

The formulations, i.e. the compositions or mixtures containing the compound of formula I (active ingredient) are prepared in known manner, e.g. by homogeneously mixing and/or grinding the active ingredients with extenders, e.g. solvents, solid carriers and, in some cases, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the active ingredient to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$-$C_{22}$), e.g. the sodium or potassium salts of oleic or stearic acid, or of natural fatty acid mixtures which can be obtained, e.g. from coconut oil or tallow oil. Further suitable surfactants are also the fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$-$C_{22}$alkyl radical which also includes the alkyl moiety of acyl radicals, e.g. the sodium or calcium salt of lignosulfonic acid, of dodecylsulfate, or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphoric acid ester of an adduct of p-nonylphenol with 4 to 14 moles of ethylene oxide; or phospholipids.

The surfactants customarily employed in the art of formulation are described e.g. in "1986 International McCutcheon's Emulsifiers and Detergents", The Manufacturing Confectioner Publishing Co., Glen Rock, New Jersey, U.S.A.

The pesticidal compositions usually contain 0.01 to 95%, preferably 0.1 to 80%, of a compound of formula I, 5 to 99.99% of a solid or liquid adjuvant, and 0 to 25%, preferably 0.1 to 25%, of a surfactant.

Whereas commercial products are preferably formulated as concentrates, the end user will normally employ dilute formulations having a concentration of 1-10,000 ppm.

The invention therefore also relates to pesticidal compositions which contain as active ingredient at least one compound of formula I, together with customary carriers and/or dispering agents.

The compositions may also contain further ingredients, such as stabilisers, antifoams, viscosity regulators, binders, tackifiers as well as fertilisers or other active ingredients for obtaining special effects.

PREPARATORY EXAMPLES

Preparation of Starting Materials and Intermediates

Example S1: Preparation of the compounds $\Delta^{14,29}$-15-hydroxymilbemycin D (formula V) and 14-hydroxy-$\Delta^{15,16}$-milbemycin D from milbemycin D In a glass irradiation apparatus, a solution of 5.56 g of milbemycin D and 0.03 g of methylene blue in 400 ml of acetonitrile is irradiated, under a stream of oxygen, with visible light for 10 hours at a temperature of 20° C. (200 watt projector lamp). The reaction mixture is then reduced with 3.9 g of triphenylphosphine at 20° C. The reaction mixture is concentrated, and the residue is chromatographed through a column of silica gel eluted with a 3:1 mixture of methylene chloride and ethyl acetate, affording 4.10 g of $\Delta^{14,29}$-5-hydroxy-milbemycin D with a melting point of 228°-229° C.; mass spectrum m/e: 572 (M+), 554.

Also obtained is 0.34 g of 14-hydroxy-$\Delta^{15,16}$-milbemycin D with a melting point of 252°-254° C.; mass spectrum m/e: 572 (M+), 554.

Example S2: Preparation of the compounds 5-keto-$\Delta^{14,29}$-15-hydroxy-milbemycin D (formula V) and 5-keto-14-hydroxy-$\Delta^{15,16}$-milbemycin D from 5-keto-milbemycin D (a) Preparation of 5-keto-milbemycin D A mixture of 1 g of milbemycin D, 2 g of activated manganese dioxide and 50 ml of anhydrous methylene chloride is stirred for 4 hours at 20°-25° C. The reaction mixture is filtered, and the filtrate is purified through a short column (about 30 cm) of silica gel, affording 1 g of yellowish amorphous 5-keto-milbemycin with a melting point of 152°-157° C.

(b)

The singulett oxidation of the 5-keto-milbemycin prepared in (a) and the further working up are effected by the method described in Example S1. After chromatography through silica gel there is obtained 0.6 g of 5-keto-$\Delta^{14,29}$-15-hydroxy-milbemycin D with a melting point of 160°-165° C.; mass spectrum m/e: 570 (M+), 552.

Also obtained are 30 mg of 5-keto-14-hydroxy-$\Delta^{15,16}$-milbemycin D with a melting point of 170°-174° C.

Example S3: Preparation of 5-keto-$\Delta^{14,29}$-15-hydroxymilbemycin D (formula V) and 5-keto-14-hydroxy-$\Delta^{15,16}$-milbemycin D from milbemycin D The oxidation with manganese dioxide as follow-up reaction of $\Delta^{14,29}$-15-hydroxymilbemycin D and 14-hydroxy-$\Delta^{15,16}$-milbemycin D obtained by the singulett oxygen oxidation of Example S1 affords, in quantitative yield, 5-keto-$\Delta^{14,29}$-15-hydroxymilbemycin D and 5-keto-14-hydroxy-$\Delta^{15,16}$-milbemycin D respectively.

Example S4: Preparation of 5-acetoxy-$\Delta^{14,29}$-15-hydroxy-milbemycin D (formula V) and 5-acetoxy-14-hydroxy-$\Delta^{15,16}$-milbemycin D from milbemycin D (a) Preparation of 5-acetoxymilbemycin D 160 mg (1.6 mM) of acetic anhydride are added to 560 mg (1.0 mM) of milbemycin D in 20 ml of pyridine, and the mixture is stirred at room temperature overnight. The pyridine is evaporated off, and the residue is taken up in 20 ml of ethyl acetate. The organic phase is shaken once with 10 ml of a 1N solution of hydrochloric acid and then with 10 ml of a saturated solution of NaHCO$_3$ and finally with 10 ml of a concentrated solution of NaCl. The organic phase is separated and dried over Na$_2$SO$_4$, filtered and concentrated affording 580 mg of 5-acetoxymilbemycin D as an amorphous, slightly yellow powder with a melting point of 115°–120° C.

The acyl derivatives, milbemycin A$_3$, milbemycin A$_4$ and the 13-desoxyavermectin derivative (R$_2$=sec-butyl) can also be prepared in analogous manner.

(b)

560 mg of 5-acetoxymilbemycin D and 20 mg of methylene blue in 40 ml of acetonitrile are treated with oxygen for 8 hours at 18°–22° C. in an irradiation apparatus (200 watt projector lamp). The reaction mixture is then reduced with 40 mg of triphenylphosphine at room temperature. The reaction mixture is concentrated, and the residue is chromatographed through a column of silica gel eluted with a 3:1 mixture of methylene chloride and ethyl acetate, affording 390 mg of 5-acetoxy-$\Delta^{14,29}$-15-hydroxymilbemycin D with a melting point of 153°–156° C.; mass spectrum m/e: 614 (M+), 596.

Also obtained are 42 mg of 5-acetoxy-14-hydroxy-$\Delta^{15,16}$-milbemycin D with a melting point of 151°–154° C.

Example S5: Preparation of $\Delta^{14,29}$-15-hydroxymilbemycin A$_4$ (formula IX) and 14-hydroxy-$\Delta^{15,16}$-milbemycin A$_4$ from milbemycin A$_4$ 540 mg (1 mM) of milbemycin A$_4$ in 100 ml of acetonitrile are oxidised with singulett oxygen in accordance with Example S1 and subsequently reduced with triphenylphosphine. Purification by flash chromatography through silica gel eluted with a 1:1 mixture of cyclohexane and ethyl acetate yields 310 mg of $\Delta^{14,29}$-15-hydroxymilbemycin A$_4$ with a melting point of 222°–225° C.; mass spectrum m/e: 558 (M+), 540.

Also obtained are 40 mg of 14-hydroxy-$\Delta^{15,16}$-milbemycin A$_4$ with a melting point of 147°–152° C.; mass spectrum m/e: 558 (M+), 540.

Example S6: Preparation of 5-dimethyl-tert-butylsilyloxy-$\Delta^{14,29}$-15-hydroxymilbemycin A$_3$ (formula V) and 5-dimethyl-tert-butylsilyloxy-14-hydroxy-$\Delta^{15,16}$-milbemycin A$_3$ from milbemycin A$_3$ (a) Preparation of 5-dimethyl-tert-butylsilylmilbemycin A$_3$ A reaction vessel is charged at room temperature with 480 mg (7 mM) of imidazole and 460 mg (3 mM) of dimethyl tert-butylchlorosilane in 20 ml of methylene chloride. With stirring, a solution of 655 mg (1.2 mM) of milbemycin A$_3$ in 10 ml of methylene chloride is slowly added dropwise, and the reaction mixture is heated overnight under reflux (~40° C.). The reaction mixture is concentrated, and the residue is purified through silica gel and dried, affording 730 mg of amorphous 5-dimethyl-tert-butylsilyloxymilbemycin A$_3$ with a melting point of 55°–60° C. Milbemycin A$_4$, milbemycin D and the 13-desoxyavemectin derivative (R$_2$=sec-butyl) can be silylated in the same manner. Methyldiphenylchlorosilane or bis(isopropyl)methylchlorosilane can also be used with advantage in this reaction.

(b)

In accordance with the procedure described in Example S4b), 550 mg of 5-dimethyl-tert-butylsilyl-$\Delta^{14,29}$-15-hydroxymilbemycin A$_3$ (m.p. 238°–240° C.; mass spectrum m/e: 658 (M+), 640) can be obtained from 720 mg of 5-dimethyl-tert-butylsilylmilbemycin A$_3$ by singulett oxygen oxidation with Bengal pink as sensitiser, and subsequent reaction of the peroxides with triphenylphosphine.

Also obtained are 42 mg of amorphous 5-dimethyl-tert-butylsilyl-14-hydroxy-$\Delta^{15,16}$-milbemycin A$_3$ with a melting point of 45°–50° C.

Example S7: Preparation of $\Delta^{14,29}$-15-hydroxymilbemycin A$_3$ (formula V) and 14-hydroxy-$\Delta^{15,16}$-milbemycin A$_3$ 120 mg of 5-dimethyl-tert-butylsilyloxy-$\Delta^{14,29}$-15-hydroxymilbemycin A$_3$ and 2 ml of a 1% solution of p-toluenesulfonic acid in methanol are stirred for 9 hours at room temperature and then treated with a 5% aqueous solution of NaHCO$_3$. After extraction with three 2 ml portions of diethyl ether, the organic phase is concentrated and the crude product is chromatographed through 20 g of silica gel eluted with a 1:12 mixture of acetone and methylene chloride, affording 67 mg of $\Delta^{14,29}$-15-hydroxymilbemycin A$_3$ with a melting point of 219°–222° C.

In corresponding manner, 38 mg of 14-hydroxy-$\Delta^{15,16}$-milbemycin A$_3$ (m.p. 128°–132° C.) are obtained from 60 mg of 5-dimethyl-tert-butylsilyloxy-14-hydroxy-$\Delta^{15,16}$-milbemycin A$_3$.

Example S8: Preparation of 29-oxo-5-acetoxy-$\Delta^{14,15\text{-}trans}$-milbemycin D (formula II) and 15-oxo-5-acetoxy-$\Delta^{14,29}$-milbemycin D (formula V)

570 mg of pyridinium dichromate are added at 10° C. to 600 mg of 15-hydroxy-5-acetoxy-$\Delta^{14,29}$-milbemycin D in 35 ml of absolute dimethylformamide, and the batch is vigorously stirred for 2 hours at room temperature. The solvent is removed under a high vacuum, the resultant resin is suspended in diethyl ether, and the suspension is filtered. The liquid phase is washed with water and a saturated solution of sodium chloride, dried over sodium sulfate and filtered. The yellowish crude product is purified by chromatography through a column of silica gel eluted with a 15:1 mixture of methylene chloride and diethyl ether, affording 330 mg of 29-oxo-5-acetoxy-$\Delta^{14,15}$-milbemycin D with a melting point of 155°–159° C. and, as by-product, 200 mg of 15-oxo-5-acetoxy-$\Delta^{14,29}$-milbemycin D with a melting point of 139°–142° C.

Example S9: Preparation of 29-oxo-$\Delta^{14,15cis}$-milbemycin D (formula II, X) and 29-oxo-$\Delta^{14,15trans}$-milbemycin D (formula II, X)

136 mg of 29-oxo-$\Delta^{14,15trans}$-5-dimethyl-tert-butylsilyloxymilbemycin D are dissolved at room temperature in 15 ml of methanol. After the addition of 2 ml of p-toluenesulfonic acid, the batch is stirred for 1 hour. The solvent is subsequently removed under a high vacuum, and the crude product is purified by chromatography through a column of silica gel eluted with a 3:1 mixture of methylene chloride and diethyl ether, affording 125 mg of the trans-product in the form of a white amorphous powder with a melting point of about 150° C. Half of this trans-product is dissolved in methanol, and several drops of dilute sulfuric acid are added. After stirring for 3 hours at about 30° C., the solvent is removed under a high vacuum, and the crude product is dissolved in methylene chloride. The resultant solution is filtered through a short column (5 cm long) of silica gel, thus affording 60 mg of the more stable cis-product, which decomposes at about 250° C.

Example S10: Preparation of 15-mesyloxy-$\Delta^{14,29}$-5-dimethyl-tert-butylsilyloxymilbemycin $A_4$ Under argon, 230 mg (2 mM) of methane sulfochloride in 2 ml of tetrahydrofuran are added at about −10° C. to a solution of 670 mg (1 mM) of 15-hydroxy-$\Delta^{14,29}$-5-dimethyl-tert-butylsilyloxymilbemycin $A_4$ and 405 mg (4 mM) of triethylamine in 40 ml of dry tetrahydrofuran. With vigorous stirring, the solution is slowly heated to about +10° C. and stirred further for 30 minutes. This intermediate prepared in situ can be further processed without purification.

Example S11: Preparation of 29-hydroxy-5-dimethyl-tert-butylsilyloxymilbemycin $A_4$ About 5.4 ml (300 mM) of water are added at about 10° C. to the $A_4$-derivative prepared in accordance with the previous Example S10, in the tetrahydrofuran reaction mixture, and the batch is stirred overnight at room temperature.

200 ml of ethyl acetate are added, and the batch is then extracted with a saturated solution of sodium chloride. After drying over a suitable drying agent, e.g. sodium sulfate, the solvent is removed in vacuo. Purification through a column of silica gel eluted with a 20:1 mixture of methylene chloride and diethyl ether affords, after freeze drying, 470 mg of the title compound with a melting point of 142°–145° C.

Example S12: Preparation of 29-hydroxymilbemycin $A_4$

If in the previous Example S11, either before or after the addition of water, the reaction mixture is acidified with p-toluenesulfonic acid or methanesulfonic acid, then this affords the title compound, which, after freeze drying, melts at 143°–147° C.

Example S13: Preparation of 29-oxo-5-(dimethyl-tert-butylsilyloxy)milbemycin $A_4$ 450 mg (0.66 mmol) of 29-hydroxy-5-(dimethyl-tert-butylsilyloxy)milbemycin $A_4$ are charged at room temperature to 60 ml of methylene chloride. Then 900 mg of manganese dioxide are added and the mixture is stirred efficiently for ca. 12 hours. After filtration, the solvent is removed under vacuum and the crude product is purified by column chromatography (silica gel; elution with a 3:1 mixture of petroleum ether/ethyl acetate). The title compound (440 mg) is obtained in the form of a white powder which melts at 250°–253° C.

Example S14: Preparation of 5,29-bis(oxomilbemycin $A_4$)

190 mg (0.34 mmol) of 29-hydroxymilbemycin $A_4$ are well stirred in 30 ml of methylene chloride at room temperature for 5 hours in the presence of 1 g of manganese dioxide. After filtration over Hyflo (cellulose), the solvent is removed by evaporation. The amorphous product (122 mg) is further processed direct.

Preparation of the Final Products

Example F1: Preparation of 5-acetoxy-29-methoximinomilbemycin D 120 mg (0.2 mmol) of 5-acetoxy-29-oxomilbemycin D and 100 mg (1.2 mmol) of methoxyamine hydrochloride are well stirred for 2 hours at room temperature in a mixture of 10 ml of abs. ethanol and 5 ml of dry tetrahydrofuran. After addition of a few drops of triethylamine, the solvent is removed under vacuum and the product is purified by column chromatography (silica gel; elution with a 10:1 mixture of methylene chloride/diethyl ether), affording 102 mg of the title compound which melts at 137°–139° C.

Example F2: Preparation of 5-(dimethyl-tert-butylsilyloxy)-29-hydroximinomilbemycin $A_4$ 335 mg (0.5 mmol) of 5-(dimethyl-tert-butylsilyloxy)-29-oxomilbemycin $A_4$, 417 mg (6 mmol) of hydroxylammonium chloride and 1 g of molecular sieve (pore size 3 Å–4 Å; sodium aluminium silicate module) are well stirred overnight at room temperature in a mixture of 40 ml of abs. ethanol and 20 ml of dry tetrahydrofuran. After filtration, the solvent is removed under vacuum and the crude product is purified by column chromatography (silica gel; elution with a 5:1 mixture of petroleum ether/ethyl acetate), affording 180 mg of the title compound as an amorphous white powder which melts at ca. 132°–172° C.

Example F3: Preparation of 29-hydroximinomilbemycin $A_4$ 135 mg (0.2 mmol) of 5-(dimethyl-tert-butylsilyloxy)-29-hydroxy-iminomilbemycin $A_4$ are stirred at room temperature in 5 ml of a 1% solution of p-toluenesulfonic acid in methanol. After addition of a few drops of triethylamine, the solvent is removed under vacuum and the crude product is purified by column chromatography (silica gel; elution with diethyl ether), affording 104 mg of the title compound as a white amorphous powder which melts at 163°–167° C.

Example F4: Preparation of 29-phenoximinomilbemycin $A_4$ 570 mg (0.85 mmol) of 5-(dimethyl-tert-butylsilyloxy)-29-oxo-milbemycin $A_4$, 725 mg (5 mmol) of O-phenylhydroxylamine hydrochloride and 2 g of molecular sieve are well stirred for 3 hours at room temperature in a mixture of 40 ml of abs. ethanol and 20 ml of dry tetrahydrofuran. After filtration, the solvent is removed under vacuum and the crude product is purified by column chromatography (silica gel; elution with a 5:1 mixture of methylene chloride/petroleum ether). The 400 mg of 5-(dimethyl-tert-butylsilyloxy)-29-phenoximinomilbemycin $A_4$ obtained are stirred for 2 hours at room temperature in a mixture of 30 ml of a 1% solution of p-toluenesulfonic acid in methanol and 15 ml of dry tetrahydrofuran. After removing the solvent under vacuum, the crude product is purified by column chromatography (silica gel; elution with a 25:1 mixture of methylene chloride/diethyl ether), affording 285 mg of the title compound as a white powder which melts at 120°–125° C.

Example F5: Preparation of 29-(tetrahydropyran-2-yl)-oximinomilbemycin A₄ and 7-tetrahydropyranyloxy-29-tetrahydropyranyloxymilbemycin A₄

275 mg (0.4 mmol) of 5-(dimethyl-tert-butylsilyloxy)-29-hydroximinomilbemycin A₄, 201 mg (2.4 mmol) of 3,4-dihydro-2H-pyrane and 3 mg of camphorsulfonic acid are well stirred at room temperature for 20 hours in 30 ml of methylene chloride. The solvent is thereafter removed under vacuum and the crude product is left to stand in the dark for 3 days in 3.5 ml of hydrogen fluoride/pyridine complex. After concentration under a high vacuum the crude product is purified by column chromatography (silica gel; elution with a 1:1 mixture of petroleum ether/diethyl ether), affording 22 mg of the disubstituted title compound and 65 mg of the monosubstituted compound. Both amorphous powders melt at 110°–115° C.

Example F6: Preparation of 5,29-bis(hydroximino)milbemycin A₄

95 mg (0.17 mmol) of 5,29-bis(oxo)milbemycin A₄, 210 mg (3 mmol) of hydroxylammonium chloride and 1 g of molecular sieve (pore size 3 Å–4 Å; sodium aluminium silicate module) are well stirred overnight at room temperature in a mixture of 20 ml of methanol and 10 ml of dry tetrahydrofuran. After filtration, the solvent is removed under vacuum and the crude product is purified by column chromatography (silica gel; elution with a 10:1 mixture of methylene chloride/diethyl ether), affording 70 mg of the title compound as an amorphous white powder which melts at ca. 184°–186° C.

The following compounds are prepared by procedures analogous to those described above:

TABLE 1

Typical representatives of intermediates of formula II
[X = —CH(OR₁)—]
[= $\Delta^{14,15trans}$—29—oxo]

| Compound | R₂ | R₁ | m.p. [°C.] |
|---|---|---|---|
| 1.1. | CH₃ | H | |
| 1.2. | C₂H₅ | H | |
| 1.3. | C₃H₇iso | H | 120–124 |
| 1.4. | C₄H₉sec | H | |
| 1.5. | CH₃ | Si(CH₃)₂C₄H₉tert | |
| 1.6. | C₂H₅ | Si(CH₃)₂C₄H₉tert | 250–253 |
| 1.7. | C₃H₇iso | Si(CH₃)₂C₄H₉tert | 215–220 |
| 1.8. | C₄H₉sec | Si(CH₃)₂C₄H₉tert | |
| 1.9. | CH₃ | C(O)CH₃ | |
| 1.10. | C₂H₅ | C(O)CH₃ | |
| 1.11. | C₃H₇iso | C(O)CH₃ | 155–159 |
| 1.12. | C₄H₉tert | C(O)CH₃ | |

This list constitutes no limitation.

TABLE 2

Typical representatives of intermediates of formula II
[X = —CH(OR₁)—]
[= $\Delta^{14,29cis}$—29—oxo]

| Compound | R₂ | R₁ | m.p. [°C.] |
|---|---|---|---|
| 2.1. | CH₃ | H | |
| 2.2. | C₂H₅ | H | amorphous ca. 60 |
| 2.3. | C₃H₇iso | H | from 250 dec. |
| 2.4. | C₄H₉sec | H | |
| 2.5. | CH₃ | Si(CH₃)₂C₄H₉tert | |
| 2.6. | C₂H₅ | Si(CH₃)₂C₄H₉tert | 212–215 |
| 2.7. | C₃H₇iso | Si(CH₃)₂C₄H₉tert | 78–83 |
| 2.8. | C₄H₉sec | Si(CH₃)₂C₄H₉tert | |
| 2.9. | CH₃ | C(O)CH₃ | |
| 2.10. | C₂H₅ | C(O)CH₃ | |
| 2.11. | C₃H₇iso | C(O)CH₃ | |
| 2.12. | C₄H₉tert | C(O)CH₃ | |

This list constitutes no limitation.

TABLE 3

Typical representatives of compounds of formula I, wherein X is —CH(OR₁)— and R₁ is hydrogen:

| Compound | R₂ | R₃ | Physical data m.p. [°C.] |
|---|---|---|---|
| 3.1 | CH₃ | H | |
| 3.2. | C₂H₅ | H | 163–167 |
| 3.3. | C₃H₇iso | H | |
| 3.4. | C₄H₉sek | H | |
| 3.5. | CH₃ | CH₃ | |
| 3.6. | C₂H₅ | CH₃ | 95–98 |
| 3.7. | C₃H₇iso | CH₃ | 125–130 |
| 3.8. | C₄H₉sec | CH₃ | |
| 3.9. | CH₃ | C₂H₅ | |
| 3.10 | C₂H₅ | C₂H₅ | 127–132 |
| 3.11 | C₃H₇iso | C₂H₅ | |
| 3.12 | C₄H₉sec | C₂H₅ | |
| 3.13 | CH₃ | C₃H₇n | |
| 3.14 | C₂H₅ | C₃H₇n | |
| 3.15 | C₃H₇iso | C₃H₇n | |
| 3.16 | C₄H₉sec | C₃H₇n | |
| 3.17 | CH₃ | C₄H₉n | |
| 3.18 | C₂H₅ | C₄H₉n | |
| 3.19 | C₃H₇iso | C₄H₉n | |
| 3.20 | C₄H₉sec | C₄H₉n | |
| 3.21 | CH₃ | C₄H₉tert | |
| 3.22 | C₂H₅ | C₄H₉tert | 110–115 |
| 3.23 | C₃H₇iso | C₄H₉tert | |
| 3.24 | C₄H₉sec | C₄H₉tert | |
| 3.25 | CH₃ | C₃H₇iso | |
| 3.26 | C₂H₅ | C₃H₇iso | |
| 3.27 | C₃H₇iso | C₃H₇iso | |
| 3.28 | C₄H₉sec | C₃H₇iso | |
| 3.29 | CH₃ | C₄H₉sec | |
| 3.30 | C₂H₅ | C₄H₉sec | |
| 3.31 | C₃H₇iso | C₄H₉sec | |
| 3.32 | C₄H₉sec | C₄H₉sec | |
| 3.33 | CH₃ | phenyl | |
| 3.34 | C₂H₅ | phenyl | 120–125 |
| 3.35 | C₃H₇iso | phenyl | |
| 3.36 | C₄H₉sec | phenyl | |
| 3.37 | CH₃ | 2-tetrahydropyranyl | |
| 3.38 | C₂H₅ | 2-tetrahydropyranyl | 110–115 |
| 3.39 | C₃H₇iso | 2-tetrahydropyranyl | |
| 3.40 | C₄H₉sec | 2-tetrahydropyranyl | |
| 3.41 | CH₃ | C₅H₁₁n | |
| 3.42 | C₂H₅ | C₆H₁₃n | |
| 3.43 | C₃H₇iso | C₅H₁₁n | |
| 3.44 | C₄H₉sec | C₆H₁₃n | |
| 3.45 | CH₃ | benzyl | |
| 3.46 | C₂H₅ | benzyl | |
| 3.47 | C₃H₇iso | benzyl | |
| 3.48 | C₄H₉sec | benzyl | |
| 3.49 | CH₃ | 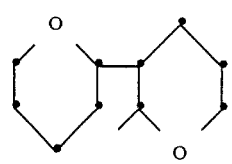 | |

TABLE 3-continued

Typical representatives of compounds of formula I, wherein X is —CH(OR₁)— and R₁ is hydrogen:

| Compound | R₂ | R₃ | Physical data m.p. [°C.] |
|---|---|---|---|
| 3.50 | C₂H₅ | (structure) | |
| 3.51 | C₃H₇iso | (structure) | |
| 3.52 | C₄H₉sec | (structure) | |

TABLE 4

Typical representatives of compounds of formula I, wherein X is —CH(OR₁)— and R₁ is a OH protective group:

| Compound | R₂ | R₃ | R₁ | Physical data m.p. [°C.] |
|---|---|---|---|---|
| 4.1. | CH₃ | H | COCH₃ | |
| 4.2. | C₂H₅ | H | COCH₃ | |
| 4.3. | C₃H₇iso | H | COCH₃ | |
| 4.4. | C₄H₉sec | H | COCH₃ | |
| 4.5. | CH₃ | CH₃ | COCH₃ | |
| 4.6. | C₂H₅ | CH₃ | COCH₃ | |
| 4.7. | C₃H₇iso | CH₃ | COCH₃ | 137–139 |
| 4.8. | C₄H₉sec | CH₃ | COCH₃ | |
| 4.9. | CH₃ | CH₃ | Si(CH₃)₂C(CH₃)₃ | |
| 4.10 | C₂H₅ | CH₃ | Si(CH₃)₂C(CH₃)₃ | 96–100 |
| 4.11 | C₃H₇iso | CH₃ | Si(CH₃)₂C(CH₃)₃ | |
| 4.12 | C₄H₉sec | CH₃ | Si(CH₃)₂C(CH₃)₃ | |
| 4.13 | CH₃ | C₂H₅ | Si(CH₃)₂C(CH₃)₃ | |
| 4.14 | C₂H₅ | C₂H₅ | Si(CH₃)₂C(CH₃)₃ | 94–97 |
| 4.15 | C₃H₇iso | C₂H₅ | Si(CH₃)₂C(CH₃)₃ | |
| 4.16 | C₄H₉sec | C₂H₅ | Si(CH₃)₂C(CH₃)₃ | |
| 4.17 | CH₃ | H | Si(CH₃)₂C(CH₃)₃ | |
| 4.18 | C₂H₅ | H | Si(CH₃)₂C(CH₃)₃ | 132–137 |
| 4.19 | C₃H₇iso | H | Si(CH₃)₂C(CH₃)₃ | |
| 4.20 | C₄H₉sec | H | Si(CH₃)₂C(CH₃)₃ | |
| 4.21 | CH₃ | 2-tetrahydropyranyl | Si(CH₃)₂C(CH₃)₃ | |
| 4.22 | C₂H₅ | 2-tetrahydropyranyl | Si(CH₃)₂C(CH₃)₃ | 90–93 |
| 4.23 | C₃H₇iso | 2-tetrahydropyranyl | Si(CH₃)₂C(CH₃)₃ | |
| 4.24 | C₄H₉sec | 2-tetrahydropyranyl | Si(CH₃)₂C(CH₃)₃ | |
| 4.25 | CH₃ | (structure) | Si(CH₃)₂C(CH₃)₃ | |
| 4.26 | C₂H₅ | (structure) | Si(CH₃)₂C(CH₃)₃ | amorphous |
| 4.27 | C₃H₇iso | (structure) | Si(CH₃)₂C(CH₃)₃ | |

TABLE 4-continued

Typical representatives of compounds of formula I, wherein X is —CH(OR$_1$)— and R$_1$ is a OH protective group:

| Compound | R$_2$ | R$_3$ | R$_1$ | Physical data m.p. [°C.] |
|---|---|---|---|---|
| 4.28 | C$_4$H$_9$sec | (structure) | Si(CH$_3$)$_2$C(CH$_3$)$_3$ | |
| 4.29 | CH$_3$ | C(CH$_3$)$_3$ | Si(CH$_3$)$_2$C(CH$_3$)$_3$ | |
| 4.30 | C$_2$H$_5$ | C(CH$_3$)$_3$ | Si(CH$_3$)$_2$C(CH$_3$)$_3$ | amorphous |
| 4.31 | C$_3$H$_7$iso | C(CH$_3$)$_3$ | Si(CH$_3$)$_2$C(CH$_3$)$_3$ | |
| 4.32 | C$_4$H$_9$sec | C(CH$_3$)$_3$ | Si(CH$_3$)$_2$C(CH$_3$)$_3$ | |
| 4.33 | CH$_3$ | phenyl | Si(CH$_3$)$_2$C(CH$_3$)$_3$ | |
| 4.34 | C$_2$H$_5$ | phenyl | Si(CH$_3$)$_2$C(CH$_3$)$_3$ | amorphous |
| 4.35 | C$_3$H$_7$iso | phenyl | Si(CH$_3$)$_2$C(CH$_3$)$_3$ | |
| 4.36 | C$_4$H$_9$sec | phenyl | Si(CH$_3$)$_2$C(CH$_3$)$_3$ | |

TABLE 5

Typical representatives of compounds of formula I, wherein X is the —C(O)— group:

| Compound | R$_2$ | R$_3$ | Physical data m.p. [°C.] |
|---|---|---|---|
| 5.1 | CH$_3$ | H | |
| 5.2. | C$_2$H$_5$ | H | |
| 5.3. | C$_3$H$_7$iso | H | |
| 5.4. | C$_4$H$_9$sec | H | |
| 5.5. | CH$_3$ | CH$_3$ | |
| 5.6. | C$_2$H$_5$ | CH$_3$ | amorphous |
| 5.7. | C$_3$H$_7$iso | CH$_3$ | |
| 5.8. | C$_4$H$_9$sec | CH$_3$ | |
| 5.9. | CH$_3$ | C$_2$H$_5$ | |
| 5.10 | C$_2$H$_5$ | C$_2$H$_5$ | |
| 5.11 | C$_3$H$_7$iso | C$_2$H$_5$ | |
| 5.12 | C$_4$H$_9$sec | C$_2$H$_5$ | |
| 5.13 | CH$_3$ | C$_3$H$_7$n | |
| 5.14 | C$_2$H$_5$ | C$_3$H$_7$n | |
| 5.15 | C$_3$H$_7$iso | C$_3$H$_7$n | |
| 5.16 | C$_4$H$_9$sec | C$_3$H$_7$n | |
| 5.17 | CH$_3$ | C$_4$H$_9$n | |
| 5.18 | C$_2$H$_5$ | C$_4$H$_9$n | |
| 5.19 | C$_3$H$_7$iso | C$_4$H$_9$n | |
| 5.20 | C$_4$H$_9$sec | C$_4$H$_9$n | |
| 5.21 | CH$_3$ | C$_4$H$_9$tert | |
| 5.22 | C$_2$H$_5$ | C$_4$H$_9$tert | |
| 5.23 | C$_3$H$_7$iso | C$_4$H$_9$tert | |
| 5.24 | C$_4$H$_9$sec | C$_4$H$_9$tert | |
| 5.25 | CH$_3$ | C$_3$H$_7$iso | |
| 5.26 | C$_2$H$_5$ | C$_3$H$_7$iso | |
| 5.27 | C$_3$H$_7$iso | C$_3$H$_7$iso | |
| 5.28 | C$_4$H$_9$sec | C$_3$H$_7$iso | |
| 5.29 | CH$_3$ | C$_4$H$_9$sec | |
| 5.30 | C$_2$H$_5$ | C$_4$H$_9$sec | |
| 5.31 | C$_3$H$_7$iso | C$_4$H$_9$sec | |
| 5.32 | C$_4$H$_9$sec | C$_4$H$_9$sec | |
| 5.33 | CH$_3$ | phenyl | |
| 5.34 | C$_2$H$_5$ | phenyl | amorphous |
| 5.35 | C$_3$H$_7$iso | phenyl | |
| 5.36 | C$_4$H$_9$sec | phenyl | |
| 5.37 | CH$_3$ | 2-tetrahydropyranyl | |
| 5.38 | C$_2$H$_5$ | 2-tetrahydropyranyl | |
| 5.39 | C$_3$H$_7$iso | 2-tetrahydropyranyl | |
| 5.40 | C$_4$H$_9$sec | 2-tetrahydropyranyl | |
| 5.41 | CH$_3$ | C$_5$H$_{11}$n | |
| 5.42 | C$_2$H$_5$ | C$_6$H$_{13}$n | |
| 5.43 | C$_3$H$_7$iso | C$_5$H$_{11}$n | |
| 5.44 | C$_4$H$_9$sec | C$_6$H$_{13}$n | |
| 5.45 | CH$_3$ | benzyl | |
| 5.46 | C$_2$H$_5$ | benzyl | |
| 5.47 | C$_3$H$_7$iso | benzyl | |
| 5.48 | C$_4$H$_9$sec | benzyl | |
| 5.49 | CH$_3$ | (structure) | |
| 5.50 | C$_2$H$_5$ | (structure) | |
| 5.51 | C$_3$H$_7$iso | (structure) | |
| 5.52 | C$_4$H$_9$sec | (structure) | |
| 5.53 | CH$_3$ | C(CH$_3$)$_3$ | |
| 5.54 | C$_2$H$_5$ | C(CH$_3$)$_3$ | amorphous |
| 5.55 | C$_3$H$_7$iso | C(CH$_3$)$_3$ | |
| 5.56 | C$_4$H$_9$sec | C(CH$_3$)$_3$ | |

TABLE 6

Typical representatives of compounds of formula I, wherein X is the —C(=N—OR) group and R is hydrogen:

| Compound | R$_2$ | R$_3$ | Physical data m.p. [°C.] |
|---|---|---|---|
| 6.1 | CH$_3$ | H | |
| 6.2. | C$_2$H$_5$ | H | 184–186 |
| 6.3. | C$_3$H$_7$iso | H | |
| 6.4. | C$_4$H$_9$sec | H | |
| 6.5. | CH$_3$ | CH$_3$ | |
| 6.6. | C$_2$H$_5$ | CH$_3$ | 143–148 |
| 6.7. | C$_3$H$_7$iso | CH$_3$ | |

TABLE 6-continued

Typical representatives of compounds of formula I, wherein X is the —C(=N—OR) group and R is hydrogen:

| Compound | $R_2$ | $R_3$ | Physical data m.p. [°C.] |
|---|---|---|---|
| 6.8. | $C_4H_9sec$ | $CH_3$ | |
| 6.9. | $CH_3$ | $C_2H_5$ | |
| 6.10 | $C_2H_5$ | $C_2H_5$ | |
| 6.11 | $C_3H_7iso$ | $C_2H_5$ | |
| 6.12 | $C_4H_9sec$ | $C_2H_5$ | |
| 6.13 | $CH_3$ | $C_3H_7n$ | |
| 6.14 | $C_2H_5$ | $C_3H_7n$ | |
| 6.15 | $C_3H_7iso$ | $C_3H_7n$ | |
| 6.16 | $C_4H_9sec$ | $C_3H_7n$ | |
| 6.17 | $CH_3$ | $C_4H_9n$ | |
| 6.18 | $C_2H_5$ | $C_4H_9n$ | |
| 6.19 | $C_3H_7iso$ | $C_4H_9n$ | |
| 6.20 | $C_4H_9sec$ | $C_4H_9n$ | |
| 6.21 | $CH_3$ | $C_4H_9tert$ | |
| 6.22 | $C_2H_5$ | $C_4H_9tert$ | |
| 6.23 | $C_3H_7iso$ | $C_4H_9tert$ | |
| 6.24 | $C_4H_9sec$ | $C_4H_9tert$ | |
| 6.25 | $CH_3$ | $C_3H_7iso$ | |
| 6.26 | $C_2H_5$ | $C_3H_7iso$ | |
| 6.27 | $C_3H_7iso$ | $C_3H_7iso$ | |
| 6.28 | $C_4H_9sec$ | $C_3H_7iso$ | |
| 6.29 | $CH_3$ | $C_4H_9sec$ | |
| 6.30 | $C_2H_5$ | $C_4H_9sec$ | |
| 6.31 | $C_3H_7iso$ | $C_4H_9sec$ | |
| 6.32 | $C_4H_9sec$ | $C_4H_9sec$ | |
| 6.33 | $CH_3$ | phenyl | |
| 6.34 | $C_2H_5$ | phenyl | 131–133 |
| 6.35 | $C_3H_7iso$ | phenyl | |
| 6.36 | $C_4H_9sec$ | phenyl | |
| 6.37 | $CH_3$ | 2-tetrahydropyranyl | |
| 6.38 | $C_2H_5$ | 2-tetrahydropyranyl | |
| 6.39 | $C_3H_7iso$ | 2-tetrahydropyranyl | |
| 6.40 | $C_4H_9sec$ | 2-tetrahydropyranyl | |
| 6.41 | $CH_3$ | $C_5H_{11}n$ | |
| 6.42 | $C_2H_5$ | $C_6H_{13}n$ | |
| 6.43 | $C_3H_7iso$ | $C_5H_{11}n$ | |
| 6.44 | $C_4H_9sec$ | $C_6H_{13}n$ | |
| 6.45 | $CH_3$ | benzyl | |
| 6.46 | $C_2H_5$ | benzyl | |
| 6.47 | $C_3H_7iso$ | benzyl | |
| 6.48 | $C_4H_9sec$ | benzyl | |
| 6.49 | $CH_3$ | (dioxane structure) | |
| 6.50 | $C_2H_5$ | (dioxane structure) | |
| 6.51 | $C_3H_7iso$ | (dioxane structure) | |
| 6.52 | $C_4H_9sec$ | (dioxane structure) | |
| 6.53 | $CH_3$ | $C(CH_3)_3$ | |
| 6.54 | $C_2H_5$ | $C(CH_3)_3$ | 153–157 |
| 6.55 | $C_3H_7iso$ | $C(CH_3)_3$ | |
| 6.56 | $C_4H_9sec$ | $C(CH_3)_3$ | |

| Formulation Examples for the compound of formula I (throughout, percentages are by weight) | | | |
|---|---|---|---|
| Wettable powders | a | b | c |
| a compound of the Tables | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| Emulsifiable concentrate | |
|---|---|
| a compound of the Tables | 10% |
| octylphenol polyethylene glycol ether (4–5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| Dusts | a | b |
|---|---|---|
| a compound of the Tables | 5% | 8% |
| talcum | 95% | — |
| kaolin | — | 92% |

Ready for use dusts are obtained by mixing the active ingredient with the carrier, and grinding the mixture in a suitable mill.

| Extruder granulate | |
|---|---|
| a compound of the Tables | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| Tablets or boluses | | |
|---|---|---|
| I | a compound of the Tables | 33.00% |
| | methyl cellulose | 0.80% |
| | highly dispersed silicic acid | 0.80% |
| | maize starch | 8.40% |

The methyl cellulose is stirred in water and allowed to swell. Then the silicic acid is stirred in to give a homogeneous suspension. The compound of formula I and the maize starch are mixed and the aqueous suspension is added to the mix, which is kneaded to a paste. This paste is granulated through a 12M sieve and the granulate is dried.

| II | crystalline lactose | 22.50% |
|---|---|---|
| | maize starch | 17.00% |
| | microcrystalline cellulose | 16.50% |
| | magnesium stearate | 1.00% |

Phases I and II are mixed and compressed to tablets or boluses.

| Injectable: A. Oily vehicle (slow release) | |
|---|---|
| a compound of the Tables | 0.1–1.0 g |
| groundnut oil to make up 100 ml | |
| a compound of the Tables | 0.1–1.0 g |
| sesame oil to make up 100 ml | |

Preparation: the active compound is dissolved in a portion of the oil, with stirring and, if necessary, gentle heating. The oily solution is cooled and then made up to the desired volume and filtered under sterile conditions through a suitable membrane filter having a pore diameter of 0.22 μm.

| B. Water-miscible solvent (average rate of release) | |
|---|---|
| a compound of the Tables | 0.1–1.0 g |
| 4-hydroxymethyl-1,3-dioxolane | 40 g |
| (glycerol formal) | |
| 1,2-propanediol to make up 100 ml | |
| a compound of the Tables | 0.1–1.0 g |
| glycerol dimethyl ketal | 40 g |
| 1,2-propanediol to make up 100 ml | |

Preparation: the active compound is dissolved in a portion of the solvent, the solution is made up to the desired volume and filtered under sterile conditions through a suitable membrane filter having a pore diameter of 0.22 μm.

| C. Aqueous solute (rapid release) | |
|---|---|
| a compound of the Tables | 0.1–1.0 g |
| polyethoxylated ricinus oil | 10 g |
| (40 units of ethylene oxide)* | |
| 1,2-propanediol | 20 g |
| benzyl alcohol | 1 g |
| water for injection to make up 100 ml | |
| a compound of the Tables | 0.1–1.0 g |
| polyethoxylated sorbitanemonooleat | 8 g |
| (20 units of ethylene oxide)** | |
| 4-hydroxymethyl-1,3-dioxolane | 20 g |
| (glycerol formal) | |
| benzyl alcohol | 1 g |
| water for injection to make up 100 ml | |

*commercially available under the designation CREMOPHOR ® EL (BASF AG);
**commercially available under the designation TWEEN ® 80 (ICI);

Preparation: the active compound is dissolved in the solvents and surfactant and the solution is made up to the desired volume and then filtered under sterile conditions through a suitable membrane filter having a pore diameter of 0.22 μm.

The aqueous systems may also preferably be used for oral and/or intraruminal administration.

BIOLOGICAL EXAMPLES

B1: Action against $L_1$ larvae of *Lucilia sericata*

1 ml of an aqueous suspension of test compound is mixed with 3 ml of a special larval culture medium at about 50° C. such that a homogeneous composition containing 250 ppm or 125 ppm is obtained. About 30 Lucilia larvae ($L_1$) are put into each test tube containing active ingredient. A mortality count is made after 4 days. Compounds of formula I, e.g. compounds 3.2, 3.6, 3.7, 3.10, 3.34 and 3.38, are 100% effective at 125 ppm.

B2: Acaricidal action against *Boophilus microplus* (Biarra strain)

Adhesive tape is applied horizontally across a PVC plate so that 10 replete female *Boophilus microplus* ticks (Biarra strain) can be affixed thereto with their backs, side by side, in a row. Each tick is injected from an injection needle with 1 μl of a liquid which contains a 1:1 mixture of polyethylene glycol and acetone, in which mixture a specific amount of test compound of 1 μg per tick is dissolved. Control ticks are injected with liquid containing no test compound. After this treatment, the ticks are detached from the support and kept in an insectarium under normal conditions at about 28° C. and 80% relative humidity until oviposition has taken place and the larvae have hatched from the eggs of the control ticks. The activity of the test compound is determined with the $IR_{90}$, i.e. the effective dose is determined at which 9 out of 10 female ticks (90%) even after 30 days lay eggs from which larvae are unable to hatch.

Compounds of formula I, e.g. compounds 3.2, 3.6, 3.7, 3.10, 3.34 and 3.38, achieve an $IR_{10}$ at 1.0 μg.

B3: Trial with sheep infected with nematodes (*Haemonchus contortus* and *Trichostrongylus colubriformis*)

The test compound is administered in the form of a suspension with a stomach probe or by intraruminal injection to sheep which have been artificially infected with *Haemonchus contortus* and *Trichostrongylus colubriformis*. One to three animals are used for each dose. Each sheep is treated only once with a single dose of 1 mg or 0.5 mg/kg of body weight. Evaluation is made by comparing the number of worm eggs excreted in the faeces of the sheep before and after treatment.

Untreated sheep infected simultaneously and in the same manner are used as controls. In comparison with untreated and infected control groups, there is no nematode infestation (=complete reduction of the number of worm eggs in the faeces) in sheep which have been treated with compounds of formula I, e.g. compounds 3.2, 3.6, 3.7, 3.10, 3.34 and 3.38.

B4: Larvicidal action against *Aëdes aegypti*

A 0.1% solution of the test compound in acetone is pipetted onto the surface of 150 ml of water in beakers in amounts sufficient to give concentrations of 10 ppm, 3.3 ppm and 1.6 ppm. After the acetone has evaporated, 30 to 40 three-day-old larvae of *Aedes aegypti* are put into each beaker. Mortality counts are made after 1, 2 and 5 days.

In this test, compounds of formula I, e.g. compounds 3.2, 3.6, 3.7, 3.10, 3.34 and 3.38, achieve complete kill of all larvae at a concentration of 1.6 ppm even after 1 day.

B.5 Milbicidal action against *Dermanyssus gallinae*

2 to 3 ml of a test solution (100, 10, 1 and 0.1 ppm of test compound) are put into a glass container which is open at the top and about 200 mites in differnt stages of development are put into this container. The container is then sealed with cotton wool and shaken uniformly for 10 minutes until the mites are completely wetted. The container is then inverted until excess test solution has been absorbed by the cotton wool.

The container is again inverted and the treated mites are kept under observation for 3 days under laboratory conditions to evaluate the effectiveness of the test compounds. Mortality is the criterion for effectiveness.

Compounds of the Preparatory Examples, e.g. compounds 3.2, 3.6, 3.7, 3.10 and 3.38, effect 100% kill at a concentration of 100 ppm.

What is claimed is:

1. A compound of the formula

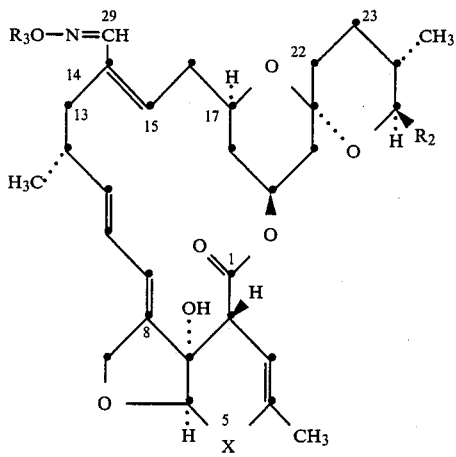

wherein

X is a group selected from —C(O)— and —C(=N—OR)—,

R is hydrogen, a OH protective group, an alkyl, cycloalkyl or acyl group, $R_2$ is methyl, ethyl, isopropyl, sec-butyl or the

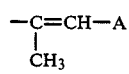

group, wherein

A is methyl, ethyl or isopropyl; and $R_3$ is hydrogen, $C_1$-$C_6$alkyl, $C_2$-$C_6$alkenyl, a radical selected from the group consisting of phenyl and benzyl which is unsubstituted or substituted by one or more members selected from the group consisting of halogen, $C_1$-$C_3$alkyl, $C_1$-$C_3$alkoxy, $C_1$-$C_3$alkylthio, $C_1$-$C_3$haloalkyl, nitro or cyano, or is the group U

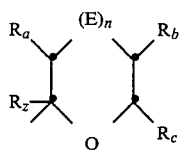

wherein n is 0, 1, 2, 3, 4 or 5, E is oxygen or —CH(R$_d$)—, $R_z$ is hydrogen, $R_a$ is hydrogen, halogen, $C_1$-$C_3$alkyl, $C_1$-$C_3$alkoxy or 2-tetrahydropyranyl, and $R_b$, $R_c$ and $R_d$ are each independently hydrogen, halogen, $C_1$-$C_3$alkyl or $C_1$-$C_3$alkoxy, which group U may also be in unsaturated form.

2. A compound of claim 1 wherein $R_2$ is methyl, ethyl, isopropyl or sec-butyl.

3. A compound of claim 1, wherein $R_3$ is hydrogen, $C_1$-$C_4$alkyl, a radical selected from the group consisting of phenyl and benzyl which is unsubstituted or substituted by one to three members of the group consisting of halogen, $C_1$-$C_2$alkyl, $C_1$-$C_2$alkylthio, $C_1$-$C_2$haloalkyl, nitro or cyano, or is the group U

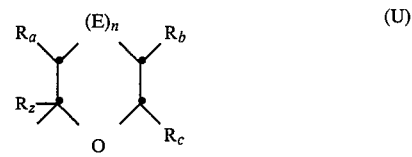

wherein n is 0 or 1, E is oxygen or $CH_2$, $R_a$ is hydrogen, fluorine, chlorine, bromine, methyl or 2-tetrahydropyranyl, and $R_b$ and $R_c$ are each independently of the other hydrogen or methyl.

4. A compound of claim 1, wherein $R_2$ is methyl.

5. A compound of claim 1, wherein $R_2$ is ethyl.

6. The compound of claim 1 named 5,29-bis(hydroxyimino)milbemycin A$_4$.

7. A composition for controlling ecto- and endoparasites of productive livestock or for controlling harmful insects, which contains, in addition to a carrier, a compound of the formula

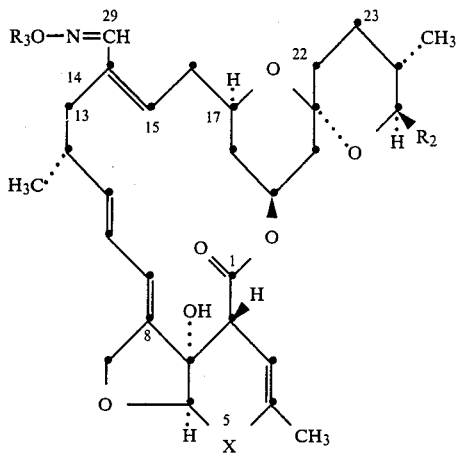

wherein

X is a group selected from —C(O)— and —C(=N—OR)—,

R is hydrogen, a OH protective group, an alkyl, cycloalkyl or acryl group, $R_2$ is methyl, ethyl, isopropyl, sec-butyl or the

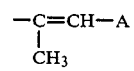

group, wherein

A is methyl, ethyl or isopropyl and $R_3$ is hydrogen, $C_1$-$C_6$alkyl, $C_2$-$C_6$alkenyl, a radical selected from the group consisting of phenyl and benzyl which is unsubstituted or substituted by one or more members selected from the group consisting of halogen, $C_1$-$C_3$alkyl, $C_1$-$C_3$alkoxy, $C_1$-$C_3$alkylthio, $C_1$-$C_3$haloalkyl, nitro or cyano, or is the group U

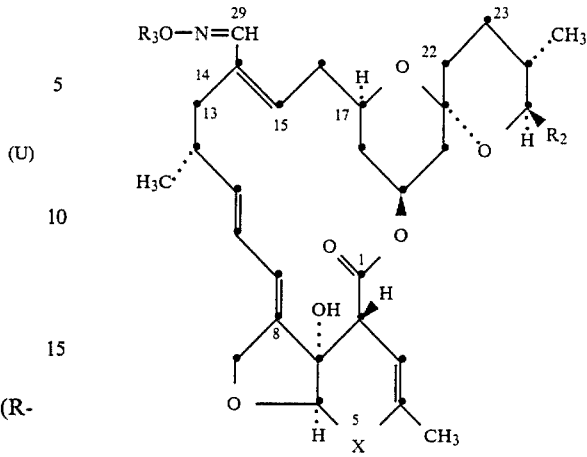

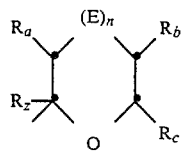

wherein n is 0, 1, 2, 3, 4 or 5, E is oxygen or —CH($R_d$)—, $R_z$ is hydrogen, $R_a$ is hydrogen, halogen, $C_1$-$C_3$alkoxy or 2-tetrahydropyranyl, and $R_b$, $R_c$ and $R_d$ are each independently hydrogen, halogen, $C_1$-$C_3$alkyl or $C_1$-$C_3$alkoxy, which group U may also be in unsaturated form.

8. A composition of claim 7, wherein $R_2$ is methyl, ethyl, isopropyl or sec-butyl.

9. A method of controlling parasites of animals or harmful insects, which comprises applying to said parasites, to said insects or to the locus thereof, an insecticidally effective amount of a compound of the formula wherein
X is a group selected from —C(O)— and —C(=N—OR)—,
R is hydrogen, a OH protective group, an alkyl, cycloalky or acyl group,
$R_2$ is methyl, ethyl, isopropyl, sec-butyl or the

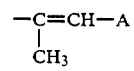

group, wherein
A is methyl, ethyl or isopropyl, and
$R_3$ is hydrogen, $C_1$-$C_6$alkyl, $C_2$-$C_6$alkenyl, a radical selected from the group consisting of phenyl and benzyl which is unsubstituted or substituted by one or more members selected from the group consisting of halogen, $C_1$-$C_3$alkyl, $C_1$-$C_3$alkoxy, $C_1$-$C_3$alkylthio, $C_1$-$C_3$haloalkyl, nitro or cyano, or is the group U

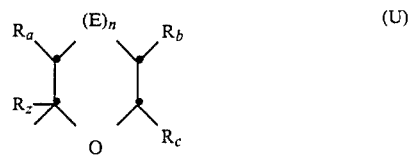

wherein n is 0, 1, 2, 3, 4 or 5, E is oxygen or —CH($R_d$)—, $R_z$ is hydrogen, $R_a$ is hydrogen, halogen, $C_1$-$C_3$alkyl, $C_1$-$C_3$alkoxy or 2-tetrahydropyranyl, and $R_b$, $R_c$ and $R_d$ are each independently hydrogen, halogen, $C_1$-$C_3$alkyl or $C_1$-$C_3$alkoxy, which group U may also be in unsaturated form.

10. A method of claim 9 wherein $R_2$ is methyl, ethyl, isopropyl or sec-butyl.

11. A method according to claim 9, wherein the parasites are nematodes.

* * * * *